US008278606B2

(12) United States Patent
Toya et al.

(10) Patent No.: US 8,278,606 B2
(45) Date of Patent: Oct. 2, 2012

(54) POCKETABLE BODY WARMER

(75) Inventors: Shoichi Toya, Hyogo (JP); Toshiki Nakasho, Hyogo (JP); Takuo Nomi, Hyogo (JP)

(73) Assignee: Sanyo Electric Co., Ltd., Osaka (JP)

( * ) Notice: Subject to any disclaimer, the term of this patent is extended or adjusted under 35 U.S.C. 154(b) by 1038 days.

(21) Appl. No.: 12/216,606

(22) Filed: Jul. 8, 2008

(65) Prior Publication Data

US 2009/0014436 A1 Jan. 15, 2009

(30) Foreign Application Priority Data

Jul. 11, 2007 (JP) ................................. 2007-182502
Jun. 17, 2008 (JP) ................................. 2008-158557

(51) Int. Cl.
*A61F 7/08* (2006.01)
*H05B 1/02* (2006.01)
*H05B 3/04* (2006.01)
*H05B 3/06* (2006.01)

(52) U.S. Cl. ........ 219/533; 219/527; 219/530; 219/536; 219/544; 219/548

(58) Field of Classification Search .................. 219/533, 219/211, 212, 527, 528, 535, 544, 549
See application file for complete search history.

(56) References Cited

U.S. PATENT DOCUMENTS 3,432,364 A * 3/1969 Balaguer ........................... 429/8
3,663,796 A * 5/1972 Hines et al. ................... 219/211
3,739,792 A * 6/1973 Holland .......................... 135/16
5,585,026 A * 12/1996 Smith et al. ................... 219/535
5,643,490 A * 7/1997 Takahashi et al. ........... 252/62.2
6,320,161 B1 * 11/2001 Hansen, Jr. ................... 219/211
8,089,030 B2 * 1/2012 Harrington et al. ........... 219/228
2008/0251400 A1 * 10/2008 Ulrich ........................ 206/315.9
2008/0272102 A1 * 11/2008 Farrington .................... 219/201

FOREIGN PATENT DOCUMENTS

CN 1977781 6/2007
JP 11-70137 3/1999
JP 2008259565 A * 10/2008

OTHER PUBLICATIONS

Chinese Office Action (with English translation) issued Sep. 29, 2011 in corresponding Chinese Patent Application No. 200810135755.7.

* cited by examiner

*Primary Examiner* — Joseph M Pelham
(74) *Attorney, Agent, or Firm* — Wenderoth, Lind & Ponack, LLP

(57) ABSTRACT

A pocketable body warmer includes: a metallic exterior casing with a metal plate being formed in the shape of a tube having a closed bottom end and an open opposite end; and a plastic interior casing with an outer contour being formed to be inserted in the metallic exterior casing. The interior casing is provided with a battery storage portion and a battery is loaded in the battery storage portion. Also, a heater is thermally connected to the metallic exterior casing for heating the metallic exterior casing.

35 Claims, 20 Drawing Sheets

POCKETABLE BODY WARMER

BACKGROUND OF THE INVENTION

1. Field of the Invention

The present invention relates to a pocketable body warmer incorporating a heater which is heated by a battery.

2. Description of the Related Art

JP-H11-70137A (1999) discloses a pocketable body warmer which has a heater operated by a battery incorporated in a casing of the body warmer. FIG. 1 shows the pocketable body warmer described in the above document. The pocketable body warmer includes a rechargeable battery 91, a heater circuit 94 having a heater 93 which is heated by electrification from the battery 91, and a casing 92 for accommodating the heater circuit 94. In the pocketable body warmer, heat is generated by the heater 93 incorporated in the casing 92, and the heater 93 is powered by the cylindrical batteries 91 loaded in parallel in the casing 92.

SUMMARY OF THE INVENTION

In the pocketable body warmer disclosed in JP-H11-70137A (1999), the casing 92 is made of a material having high thermal conductivity in order to efficiently conduct the heat, generated by the heater 93, to the entirety of the casing 92. It should be noted, however, that the casing 92 with high thermal conductivity is prone to conduct the heat also to the battery 91 loaded in the casing. The illustrated pocketable body warmer has the rechargeable battery 91 incorporated in the casing 92, but it is not always desirable for the battery 91 incorporated in the casing 92 to be heated by the heater 93. For example, it is never desirable for a nickel-hydrogen battery, being a rechargeable battery, to be used in a highly heated state for a long period of time. In view of this situation, there is a trade-off between two factors, namely, efficient conduction of the heat generated by the heater and reduced conduction of the heat to the battery loaded in the casing. Such mutually contradictory properties cannot be easily satisfied at the same time.

Further, in general, a casing of a pocketable body warmer can be efficiently heated in its entirety by thinning the entire casing to increase its thermal conductivity, but such thinly formed casing will have a weaker physical strength. Conversely, when the strength is increased by a thick formation, the entirety of the casing cannot be efficiently heated due to decreased thermal conductivity. As such, the casing of the pocketable body warmer is required to efficiently conduct the heat, generated by the heater, over the entire surface as well as to be so structured as to have the increased strength.

The present invention has been made to overcome the above-mentioned problems. It is the primary object of the present invention to provide a pocketable body warmer which can prevent the battery from an adverse influence caused by the heat. This can be realized by efficiently conducting the heat, generated by the heater, to the entire surface of the casing while reducing the thermal conduction to the battery loaded in the casing.

It is another important object of the present invention to provide a pocketable body warmer in which the entire surface of the casing is efficiently heated while the strength of the casing can be increased.

In order to achieve the above-described objects, the pocketable body warmer of the present invention is configured as follows.

The pocketable body warmer includes a metallic exterior casing 2 with a metal plate being formed to a tube having a closed bottom end and an open opposite end, a plastic-made interior casing 3 with an outer contour being formed to be inserted in the metallic exterior casing 2 and provided with a storage portion 5, a battery 1 loaded in the interior casing 3, and a heater 4 thermally connected to the metallic exterior casing 2 for heating the metallic exterior casing 2.

The above-described pocketable body warmer carries the advantage that, while the heat, generated by the heater, is efficiently conducted over the entire surface of the casing, the adverse influence by the heat on the battery loaded in the casing can be reduced. This is possible because the pocketable body warmer is so constructed and arranged that the plastic-made interior casing is accommodated in the tubular metallic exterior casing with the closed bottom end and the open opposite end, and the metallic exterior casing being thermally connected is heated by the heater which is heated by the battery loaded in the interior casing. Since the metallic exterior casing is heated by the heater, the thermal conduction can efficiently heat the entire surface of the pocketable body warmer. Further, since the plastic-made interior casing is accommodated in the metallic exterior casing and the battery is loaded in the interior casing, the battery can be maintained in a desirable thermal environment because the battery is protected from the heat coming from the metallic exterior casing which is heated by the heater. In particular, since the interior casing is made of a plastic material, the thermal conduction from the metallic exterior casing is restrained to prevent the battery from a temperature increase. That is to say, since the battery is not directly heated by the heater and the heat conducted via the metallic exterior casing is restrained by the interior casing, the battery is protected by effectively hampering the battery temperature from becoming abnormally high. In addition, since the interior casing is made of an insulation plastic material, the battery can be advantageously disposed in isolation from the metallic exterior casing and the heater.

Further, since the above-described pocketable body warmer is so structured as to accommodate the interior casing inside the metallic exterior casing, the pocketable body warmer carries the advantage that, while the metallic exterior casing is formed with a thin metal plate, the plastic-made interior casing is accommodated inside the exterior casing to obtain the entire strength. In particular, while the metallic exterior casing formed with the metal plate is formed to be thin to allow the heat generated by the heater to be quickly conducted, the metallic exterior casing can be protected by the interior casing accommodated in the metallic exterior casing. Therefore, in such pocketable body warmer, the entire surface of the casings can be efficiently heated and the strength of the casings can be enhanced.

The pocketable body warmer of the present invention can be so structured as to detachably load the battery 1 in the interior casing 3. Further, the battery 1 can be an AA size battery.

In the above-described pocketable body warmer, when the residual capacity of the battery becomes small, a period of use can be prolonged by replacement with a spare battery. In particular, when the battery is an AA size battery, a commercially available primary battery can also be used in addition to a recharged secondary battery. Thus, even when a spare battery is used up, the period of use can be prolonged by using a primary battery which can be readily procured.

Further, the pocketable body warmer of the present invention can be so structured that the interior casing 3 includes a major body portion 3A fixed to the metallic exterior casing 2, and a lid 3B detachably connected to the major body portion 3A to close an opening 20 of the metallic exterior casing 2. In this pocketable body warmer, the lid 3B is detached for replacement of the battery 1.

The above-described pocketable body warmer carries the advantage that the battery loaded in the interior casing can be replaced. This is possible because the interior casing of the pocketable body warmer includes the major body portion fixed to the metallic exterior casing, and the lid, detachably connected to the major body portion, for closing the opening of the metallic exterior casing, and thus the battery is replaced by detaching the lid. In particular, since the pocketable body warmer is so designed as to fix the battery-loading interior casing to the metallic exterior casing and to permit replacement of the battery at the opening of the metallic exterior casing, the battery replacement can be performed without taking the interior casing out of the metallic exterior casing. Therefore, the pocketable body warmer also carries the advantage that while the battery can be replaced easily and readily, the battery can be replaced safely without removing components, such as the heater, which are mounted to the interior casing.

Further, in the pocketable body warmer of the present invention, the heater 4 can be a PTC element disposed in the bottom of the metallic exterior casing 2.

The above-described pocketable body warmer carries the advantage that, since the heat is supplied by the PTC element, the temperature can be set by the PTC element itself for safe use. This is possible because, when the temperature rises to a predetermined temperature after electrification, followed by a rapid increase in electrical resistance, the PTC element substantially shuts down a current flow. In the pocketable body warmer, when the PTC element controls the temperature to be lower than the predetermined temperature, the maximal temperature can be made lower than the predetermined temperature with a simplified structure instead of using a control circuit for controlling the temperature.

The pocketable body warmer carries the additional advantage that, since the PTC element is disposed in the bottom of the metallic exterior casing, the heat generated by the heater can be efficiently conducted from the bottom portion to the side surfaces of the metallic exterior casing to heat the entirety of the metallic exterior casing quickly and uniformly. In particular, because the bottom portion of the metallic exterior casing is a portion which is less likely to be deformed by a shock occurring like when the pocketable body warmer is dropped, the structure of disposing the heater in such portion enables the heater and the inner surface of the metallic exterior casing to be maintained in a stable state of thermal connection, resulting in securely heating the metallic exterior casing for a long period of time.

Further, the pocketable body warmer of the present invention can be so structured that the heater 4 is disposed between the metallic exterior casing 2 and the interior casing 3 and that a holder plate 6 is disposed between the interior casing 3 and the heater 4. The heater 4 is interposed between the holder plate 6 and the inner surface of the metallic exterior casing 2 to thermally connect the heater 4 to the metallic exterior casing 2. A gap 60 is also defined between the holder plate 6 and the interior casing 3 to restrain thermal conduction from the heater 4 to the interior casing 3.

The above-described pocketable body warmer is featured in that the heater can unfailingly be thermally connected to the metallic exterior casing. Further, in the pocketable body warmer, since the gap is defined between the holder plate and the interior casing, the thermal conduction from the heater to the interior casing is restrained, so that the interior casing can be effectively prevented from heating the battery loaded in the interior casing.

Furthermore, in the pocketable body warmer of the present invention, the battery 1 can be a nickel-hydrogen battery.

In the pocketable body warmer, the surface of the metallic exterior casing can be ideally heated while the nickel-hydrogen battery, which is vulnerable to heat, is protected from the heat conducted from the metallic exterior casing.

Further, the pocketable body warmer of the present invention carries the advantage that disposition of the heater inside the opposite surfaces of the metallic exterior casing enables the opposite surfaces of the metallic external casing to be heated efficiently and quickly by the interior heater.

Further, the pocketable body warmer of the present invention carries the advantage that disposition of a temperature sensor proximately to or in contact with the inner side of the metallic exterior casing enables the temperature outside the metallic exterior casing to be controlled in an optimal range of temperatures while detecting the temperature very sensitively by means of a temperature sensor.

Further, in the pocketable body warmer of the present invention, the interior casing includes the major body portion fixed to the metallic exterior casing, and the lid, detachably connected to the major body portion, for closing the opening of the metallic exterior casing. The body warmer is so structured as to electrically connect, via a pin jack, the major body portion and the lid, with such simple structure enabling the major body portion and the lid to be detachably connected for achieving an electrical connection.

Further, the pocketable body warmer of the present invention is so structured that the lid is provided with a lid-side contact point in contact with an electrode of the battery loaded in the major body portion. The lid-side contact point is unfailingly in contact with the battery electrode in a state where the opening of the metallic exterior casing is closed by the lid, and thus the battery can be electrically connected to the lid.

The above and further objects of the present invention as well as the features thereof will become more apparent from the following detailed description to be made in conjunction with the accompanying drawings.

DETAILED DESCRIPTION OF THE PREFERRED EMBODIMENT(S)

Figure 1:
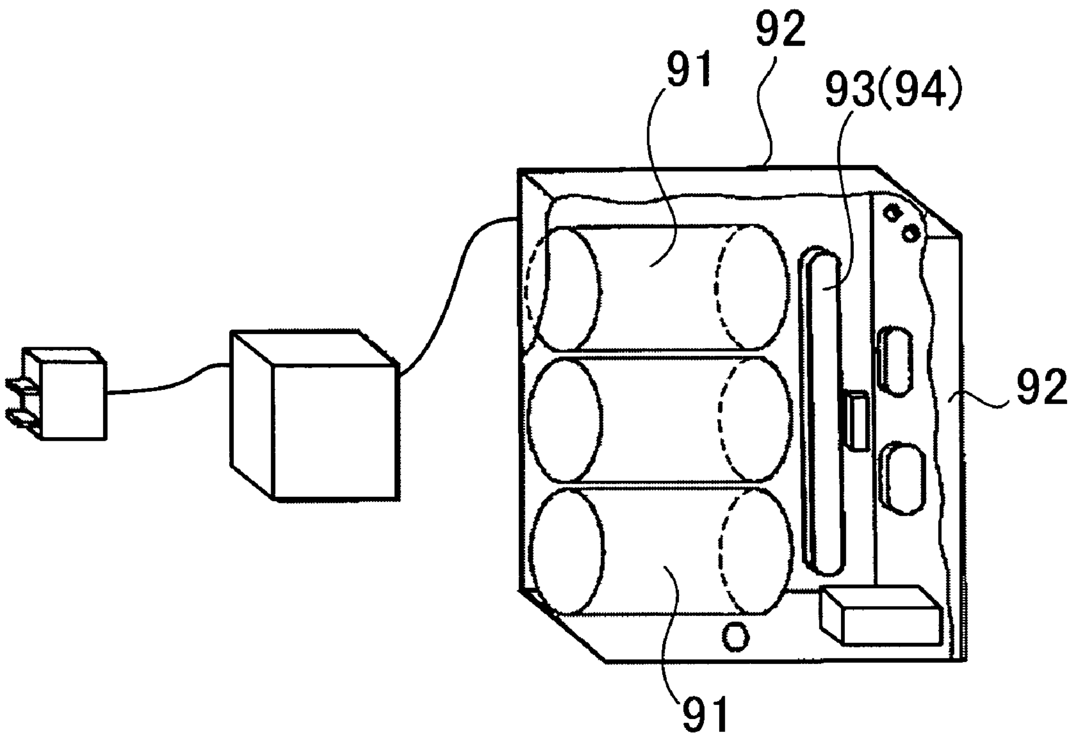
FIG.1 PRIOR ART
FIG. 1 is a perspective view showing an interior structure of a related pocketable body warmer.
Figure 2:
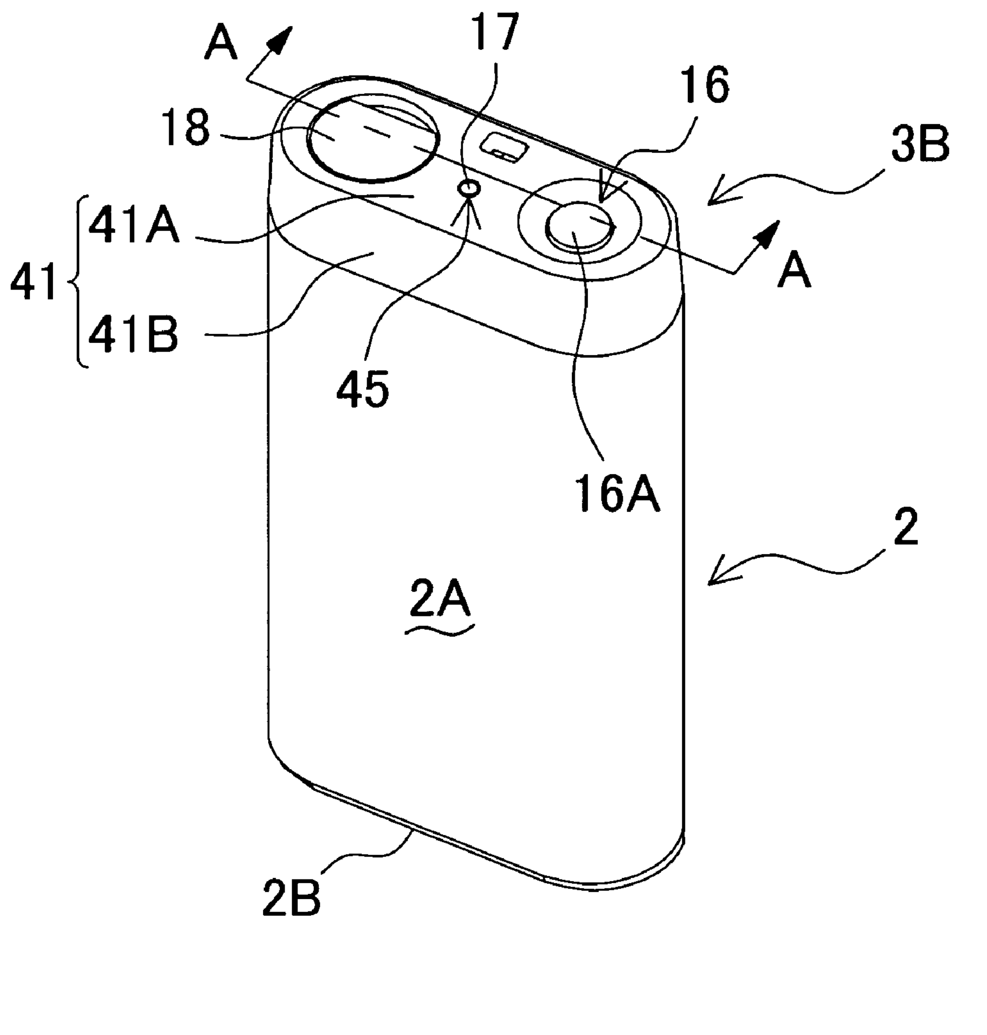
FIG. 2 is a perspective view of the pocketable body warmer in accordance with an embodiment of the present invention.

In the pocketable body warmer of the present invention, a heater 104 can be disposed inside opposite surfaces of a metallic exterior casing 102.

Also in the pocketable body warmer of the present invention, a temperature sensor 152 can be disposed proximately to or in contact with the inner side of the metallic exterior case 102.

Further, in the pocketable body warmer of the present invention, an interior casing 3, 103 respectively includes a major body portion 3A, 103A fixed to the metallic exterior casing 2, 102, and a lid 3B, 103B, detachably connected to the major body portion 3A, 103A, for closing an opening 20, 120 of the metallic exterior casing 2, 102, and the major body portion 3A, 103A and the lid 3B, 103B are electrically connected via a pin jack 13, 113.

Further, in the pocketable body warmer of the present invention, the lid 3B, 103B is provided with a lid-side contact point 12, 112 to be in contact with an electrode of a battery 1, 101 loaded in the major body portion 3A, 103A.

The pocketable body warmer shown in FIG. 2 through FIG. 12 respectively includes the metallic exterior casing 2 made of a metal plate formed in the shape of a tube having a closed bottom end and an open end, the plastic-made interior casing 3 formed with an outer contour to be disposed inside the metallic exterior casing 2 and provided with a battery storage portion 5, the battery 1 loaded in the interior casing 3, and a heater 4, thermally connected to the metallic exterior casing 2, for heating the metallic exterior casing 2.

Metallic Exterior Casing

The metallic exterior casing 2 is formed in the shape of a tube having one end of a tubular cylinder 2A closed by a bottom plate 2B and the other end being open. The metallic exterior casing 2 is made by pressing the metal plate in order to realize an excellent thermal conduction. The metal plate to be used includes an aluminum plate. However, the metal plate to be used for the metallic exterior casing can include an iron plate, a copper plate, and a brass plate. Further, the metallic exterior casing can also have countless concavities and convexities on the surface. The pocketable body warmer with such countless concavities and convexities on the surface carries the advantage that disorders associated with a low temperature can be prevented.

Figure 4:
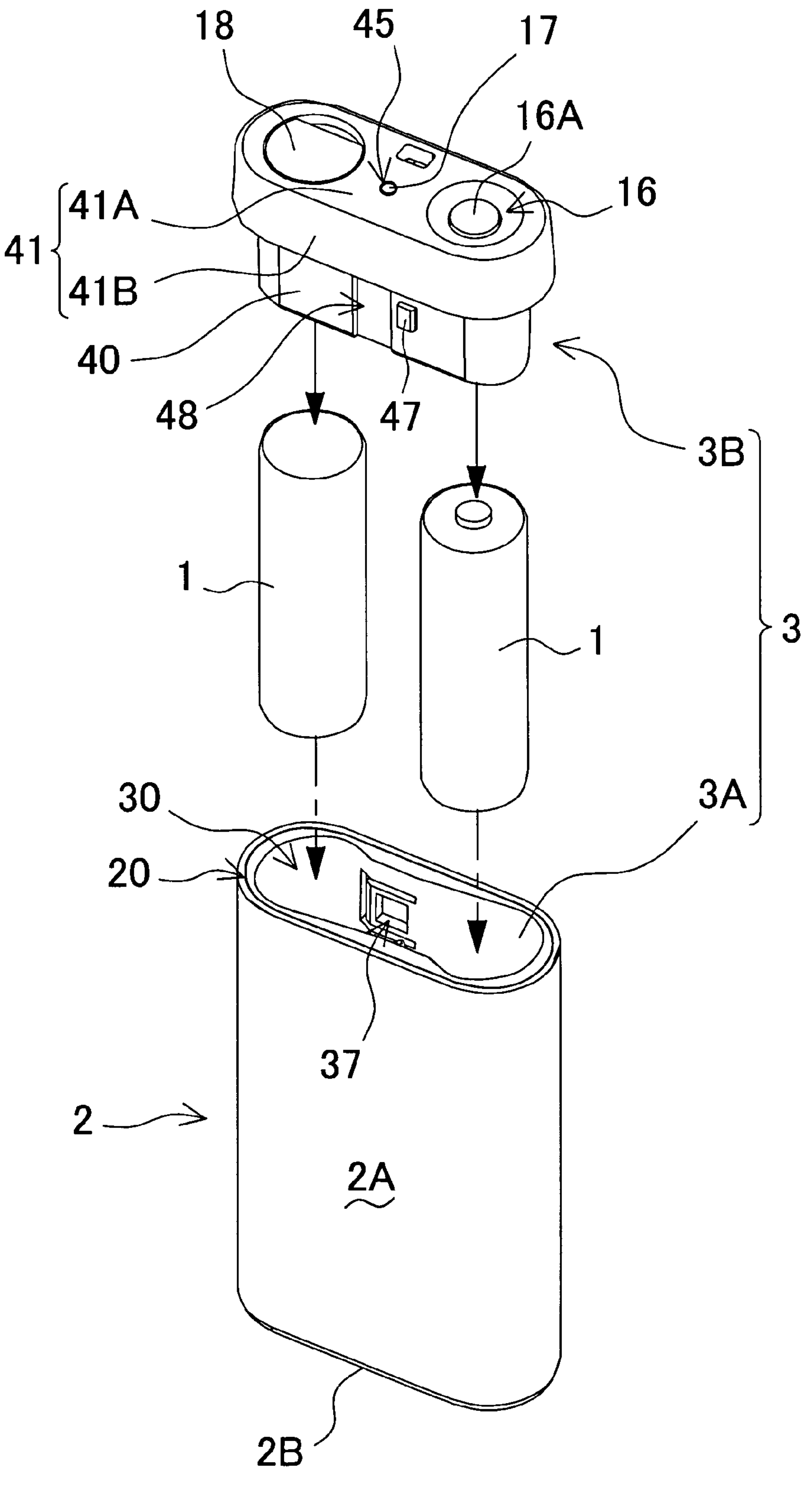
FIG. 4 is an exploded perspective view of the pocketable body warmer shown in FIG. 2.
Figure 5:
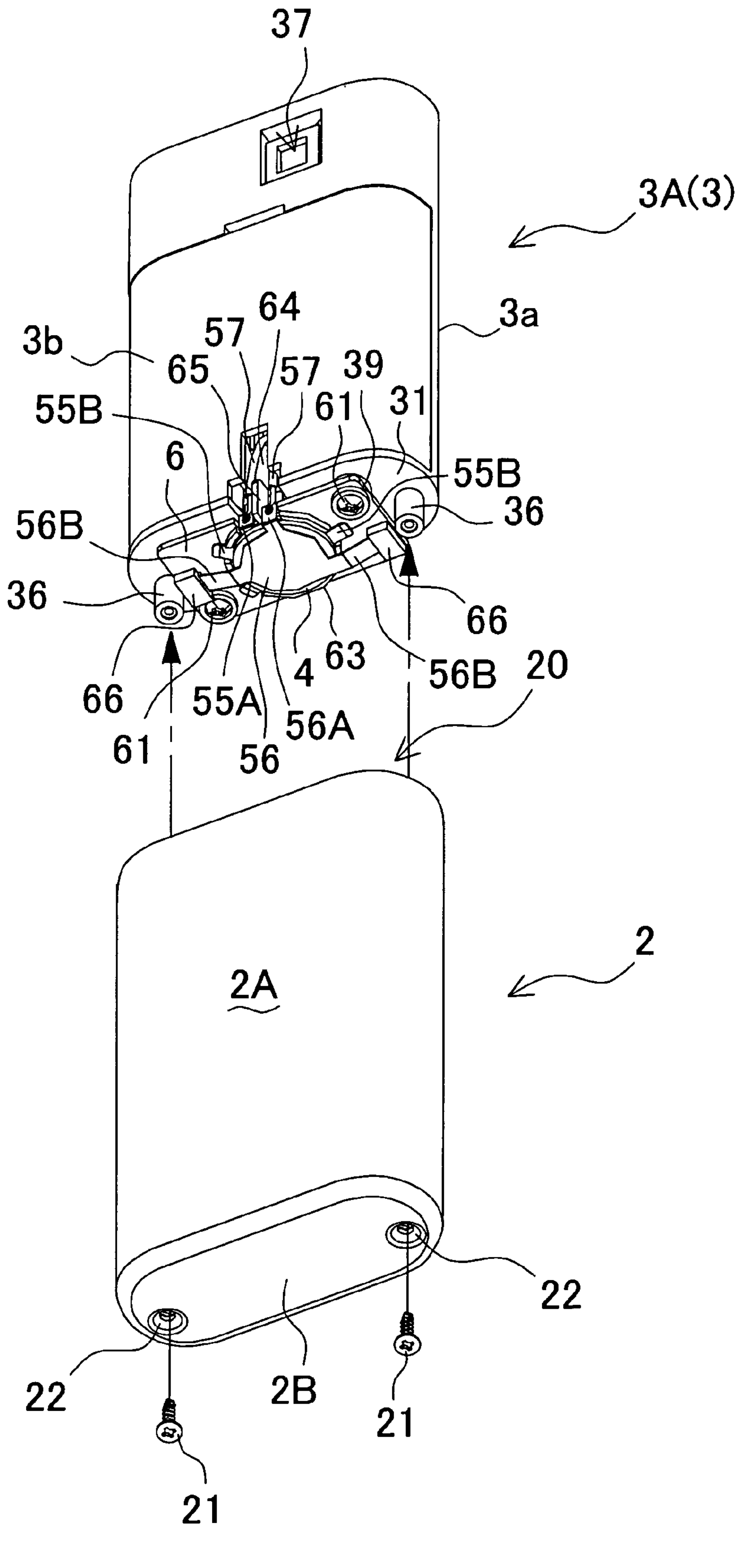
FIG. 5 is an exploded perspective view showing the connection structure between the metallic exterior casing and the interior casing of the pocketable body warmer shown in FIG. 4.

As shown in FIG. 4 and FIG. 5, the tubular metallic exterior casing 2 allows the interior casing 3 to be inserted inside from the opening 20 at one side, and the battery 1 to be loaded in the interior casing 3. Since the illustrated pocketable body warmers respectively allow two cylindrical batteries 1 to be loaded in parallel, the metallic exterior casing 2 and the interior casing 3 are made tubular with their transverse cross sections being elliptical. It should be noted, however, that the metallic exterior casing and the interior casing loaded with two cylindrical batteries in parallel can also be made tubular with their transverse cross section being oval. These pocketable body warmers have the feature that an area of contact in the tubular side surface can be made sufficiently wide. Further, although not shown, a pocketable body warmer allowing a single cylindrical battery to be loaded can have the metallic exterior casing and the interior casing being made tubular with their transverse cross sections being circular.

However, the pocketable body warmer can also be adapted to allow a rectangular battery to be loaded. Accordingly, such pocketable body warmer can have the metallic exterior casing and the interior casing shaped to receive the rectangular battery.

Interior Casing

The interior casing 3, being inserted in the metallic exterior casing 2, has the battery 1 loaded inside. The interior casing 3 is made of a plastic material having a smaller thermal conduction than does a metallic material in order to protect the loaded battery 1 from the heat coming from the metallic exterior casing 2 which is heated by the heat generated by the heater 4 or directly heated by the heater 4. Further, the loaded battery 1 is isolated from the metallic exterior casing 2 and the heater 4 by fabricating the interior casing 3 of an insulating plastic material. The illustrated interior casing 3 includes the major body portion 3A, fixed to the metallic exterior casing 2, for receiving the battery 1, and the lid 3B, detachably connected to an opening 30 of the major body portion 3A, for closing the opening 20 of the metallic exterior casing 2.

Figure 6:
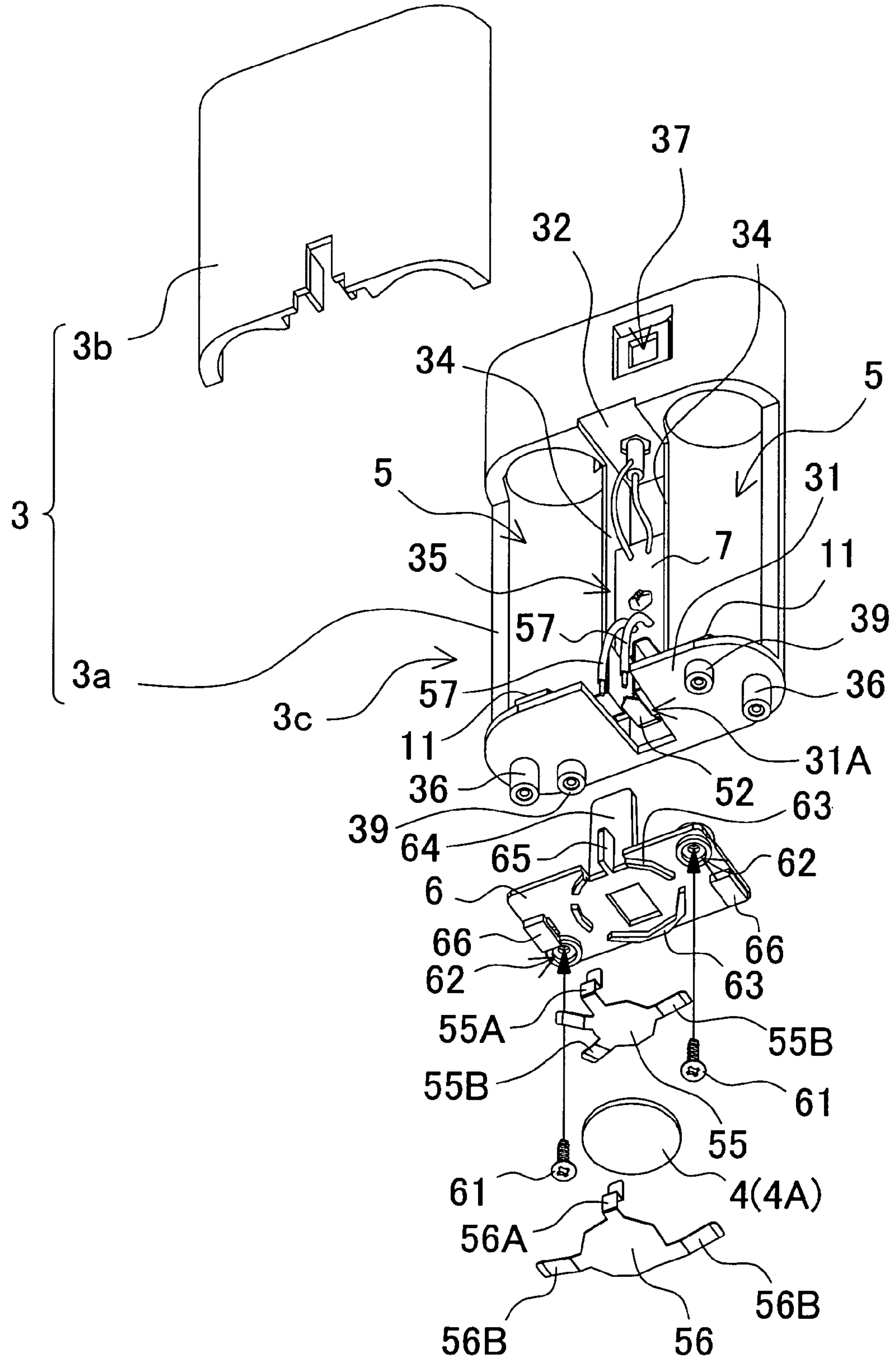
FIG. 6 is an exploded perspective view of the major body portion of the interior casing shown in FIG. 5.
Figure 7:
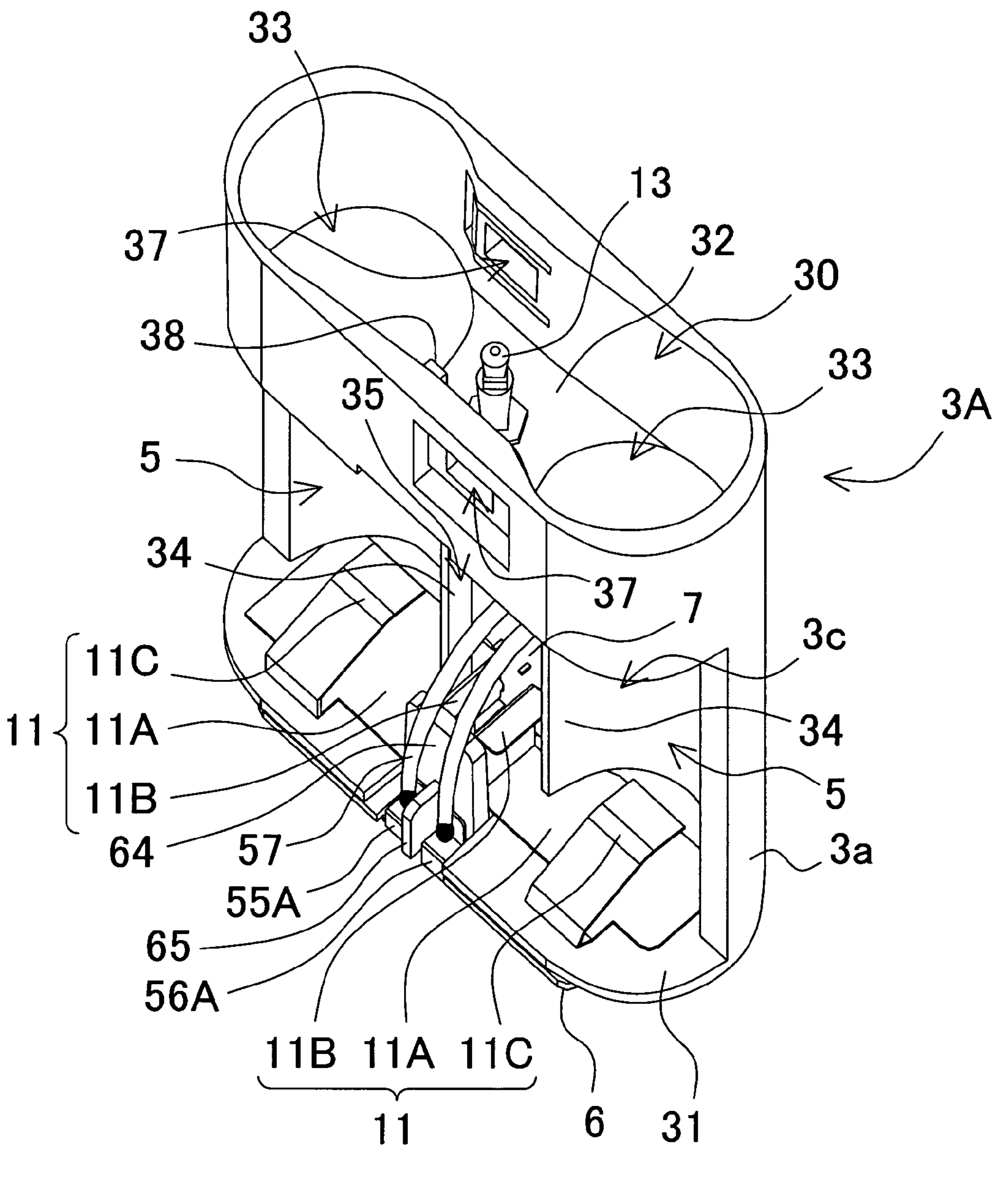
FIG. 7 is a top perspective view of the major body portion of the interior casing shown in FIG. 6.
Figure 8:
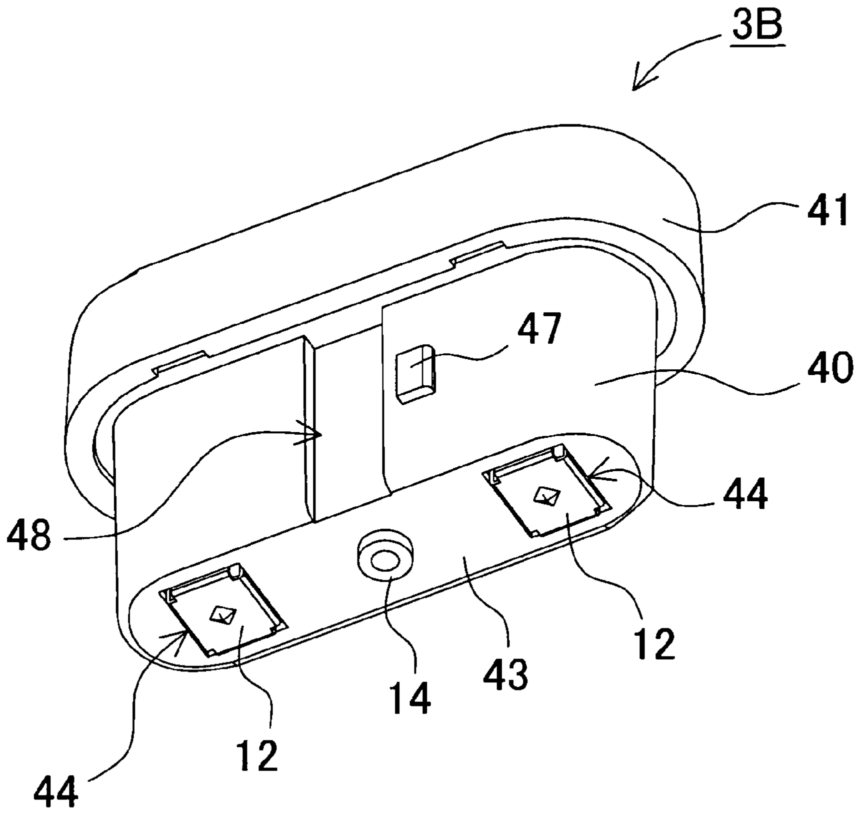
FIG. 8 is a bottom perspective view of the lid of the interior casing.

As shown in FIG. 5 through FIG. 7, the major body portion 3A has its entire shape formed to be in a tubular state facing along the inner surface of the metallic exterior casing 2, and is also provided inside with storage portions 5 for receiving the batteries 1. The illustrated major body portion 3A is designed to hold two cylindrical batteries 1, with the storage portions 5 being provided in two rows. The exterior profile of the major body portion 3A is generally equal to the interior profile of the metallic exterior casing 2, somewhat smaller to be exact, and the major body portion 3A is fitted inside the metallic exterior casing 2 to be disposed in a predetermined position. The illustrated major body portion 3A is formed as a tube with a bottom plate 31 at one end and an opening at the other end so as to allow the battery 1 to be loaded from the opening 30. As shown in FIG. 7, the major body portion 3A is provided with an intermediate wall 32 disposed inside the opening 30 at a remote location from the opening 30 to be parallel with the opening end, and insertion openings 33 of the storage portion 5 are respectively opened on both sides of the intermediate wall 32 to load the battery 1. As will be described below in detail, the pin jack 13 is protruded between the two insertion openings 33. The pin jack 13 is inserted into and connected to a pin terminal 14 provided at an insertion tube 40 of the lid 3B.

The illustrated major body portion 3A is provided with side-by-side storage portions 5 located on both sides of the major body portion 3A. The storage portions 5 of the major body portion 3A are formed as a tube to mate with along the external profile of the cylindrical battery 1 to dispose each of the loaded batteries 1 in a predetermined position. The illustrated major body portion 3A has two storage portions 5, being disposed on both sides, segmented with two partition walls 34. Each of the partition walls 34 has a curved surface, at its surface facing the battery, to mate with and along the circumferential surface of the battery 1. Further, the major body portion 3A is provided with a board storage portion 35 between the partition walls 34 for disposing a circuit board 7. That is to say, the major body portion 3A is provided with the board storage portion 35 located between the two batteries 1 loaded in a mutually parallel relationship. The circuit board 7 disposed in the major body portion 3A is connected to the battery 1 and the heater 4, and is mounted with electronic components (not shown) which actualize a circuit for controlling a power supply to the heater 4. The circuit board 7 is fixed via a set screw 28 to a fixture boss 29 provided in the board storage portion 35.

Figure 9:
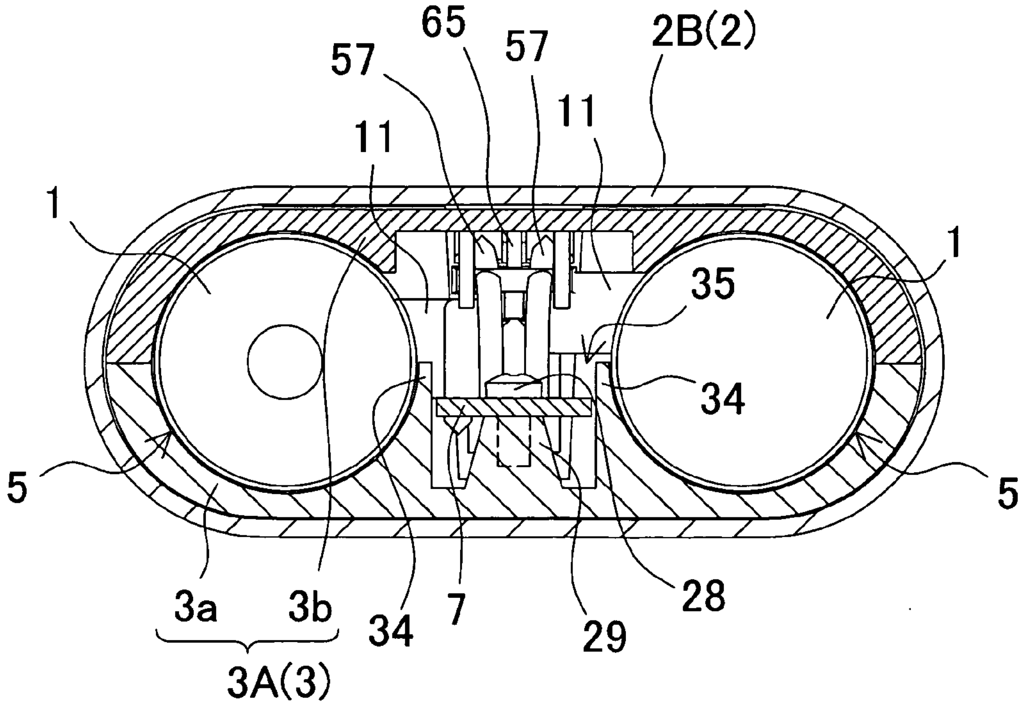
FIG. 9 is a cross-sectional view, taken along line A-A, of the pocketable body warmer shown in FIG. 3.

Further, the major body portion 3A is so structured as to enable the side face to be opened in order to dispose the circuit board 7 in the board storage portion 35. The major body portion 3A in FIG. 6 includes a major body portion case 3*a* with a tubular side surface being open, and a lid case 3*b* closing a side surface opening 3*c* of the major body portion case 3*a*. The major body portion 3A opens the side surface opening 3*c* by removing the lid case 3*b* from the major body portion case 3*a* for ease of fixture and wire connection of the circuit board 7 to the board storage portion 35. The lid case 3*b* has an inner shape formed to extend along the circumferential surface of the battery 1, as shown in FIG. 9.

Further, the major body portion 3A is provided with a case-side contact point 11, positioned at an end face of the storage portion 5, for contacting with one-side electrode of the battery 1. The case-side contact point 11 is disposed on the inner surface of the bottom plate 31 of the major body portion 3A and electrically connected to the electrode of the battery 1 loaded in the storage portion 5. The case-side contact point 11 shown in FIG. 7 and FIG. 11, respectively, is processed by folding an elastic metal plate, and includes a fixture portion 11A fixed to the inner surface of the bottom plate 31, a connection portion 11B extended from the fixture portion 11A and connected to the circuit board 7, and an elastic contact point 11C folded from the fixture portion 11A toward the electrode of the battery 1 to elastically press the electrode of the battery 1. The illustrated elastic contact point 11C has the contact point with the electrode of the battery 1, the contact point being folded to form a peak shape. Thus, the case-side contact point 11 provided with the elastic contact point 11C to elastically press the electrode of the battery 1 is featured in that, when in a pressed state toward the electrode of the battery 1 loaded in the storage portion 5, a secure electrical connection can be established.

Figure 3:
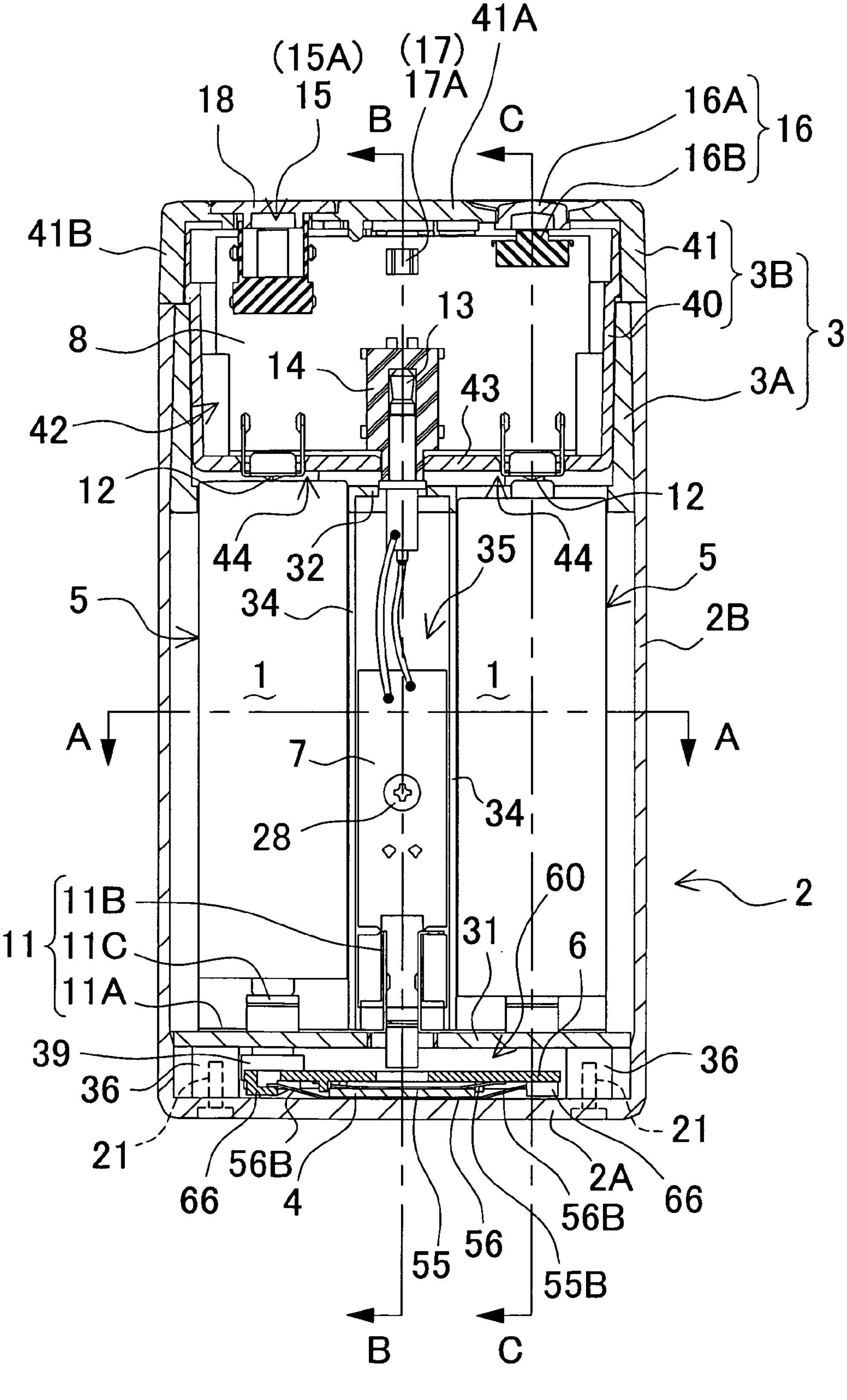
FIG. 3 is a cross-sectional view of the pocketable body warmer shown in FIG. 2.

In the above-described major body portion 3A, as shown in FIG. 3 through FIG. 5, the side closed by the bottom plate 31 is inserted into the metallic exterior casing 2 to position the opening 30 at the opening 20 of the metallic exterior casing 2, and is connected to the metallic exterior casing 2. Further, the major body portion 3A is fixed to the metallic exterior casing 2 by a set screw 21 so as not to come out loosely in a state of being inserted in the metallic exterior casing 2. The major body portion 3A is provided with a connection boss 36 into which the set screw 21 is threaded, the boss protruding from the bottom plate 31 and being integrally formed with the opposite sides of the bottom plate 31. The metallic exterior casing 2 has a through hole 22 defined respectively on opposite sides of the bottom plate 2B to allow the set screw 21 to be inserted into the through hole. The set screw 21 extending through the bottom plate 2B is threaded into the connection boss 36 of the major body portion 3A to fix the major body portion 3A to the metallic exterior casing 2.

Further, the major body portion 3A has the heater 4 fixed to the bottom plate 31 in order to dispose, in a thermally connected state, the heater 4 inside the bottom plate 2B of the metallic exterior casing 2. The major body portion 3A shown in FIG. 5 and FIG. 6 has the holder plate 6 fixed to the bottom plate 31 while positioning the heater 4 to be fixed, and has the heater 4 disposed via the holder plate 6 proximately to the bottom plate 2B of the metallic exterior casing 2.

The lid 3B, as shown in FIG. 3, FIG. 8, FIG. 10 and FIG. 11, respectively includes an insertion tube 40 to be inserted into the opening 30 of the major body portion 3A, and a flange 41 connected to the end of the insertion tube 40 to close the opening 30 of the major body portion 3A and the opening 20 of the metallic exterior casing 2. The illustrated lid 3B has a hollow board storage portion 42 inside, where a circuit board 8 is disposed.

The insertion tube 40 is formed to have an outer contour to mate with and along the inner contour of the opening 30 of the major body portion 3A so as to be able to be inserted into the opening 30 of the major body portion 3A. Further, the insertion tube 40 is provided, at an end face on the side to be inserted into the major body portion 3A, with a lid-side contact point 12 for contacting the other electrode of the battery 1 loaded in the storage portion 5. The insertion tube 40 has contact windows 44 opened on opposite sides of an end plate 43 being the end surface of the battery side, and has the lid-side contact point 12 exposed from the contact windows 44. Further, the insertion tube 40 is provided with an exposed pin terminal 14 positioned between the contact windows 44 for inserting the pink jack 13 protruding from the intermediate wall 32 of the major body portion 3A. The lid-side contact point 12 and the pin terminal 14 are fixed to the circuit board 8 disposed inside the lid 3B. In the lid 3B, when the insertion tube 40 is inserted into the opening 30 of the major body portion 3A, the lid-side contact point 12 disposed on the end plate 43 is allowed to contact the other electrode of the battery 1 for electrical connection, and the pin jack 13 protruding from the intermediate wall 32 of the major body portion 3A is inserted into the pin terminal 14 at the center of the end plate 43 to connect the circuit board 8 of the lid 3B to the circuit board 7 of the major body portion 3A.

The flange 41 is cap-shaped with a peripheral wall 41B around the top plate 41A serving as an operation surface. In a state of connecting the lid 3B to the major body portion 3A, the flange 41 is shaped to allow the outer contour of the peripheral wall 41B to match with and along the outer contour of the metallic exterior casing 2, so as to be able to close the opening 20 of the metallic exterior casing 2. The lid 3B shown in FIG. 8, FIG. 10 and FIG. 11 respectively connects the opening end of the tubular insertion tube 40 to the inner side of the peripheral wall 41B of the flange 41. Regarding the lid 3B, a protruded amount of the insertion tube 40 protruding from the flange 41 is an inserted amount into the opening 30 of the major body portion 3A. Therefore, in the lid 3B, the protruded amount of the insertion tube 40 is so designed that a contact is securely made while the electrode of the battery 1 is pressed from opposite sides between the lid-side contact point 12 of the insertion tube 40 and the case-side contact point 11 of the major body portion 3A. The illustrated insertion tube 40 and flange 41 are mutually connected in an engagement structure. However, the insertion tube and the flange can also be connected together by adhesive or thread-screwing method.

The above-described lid 3B, in a state of being inserted in the opening 30 of the major body portion 3A, is detachably connected to the major body portion 3A. The lid 3B and the major body portion 3A are connected in an engagement structure so as to be detachably connected. The illustrated lid 3B is provided with an engagement protrusion 47 around the peripheral surface of the insertion tube 40, and the major body portion 3A is provided, on the inner surface of the opening 30, with an engagement portion 37 for engagement with the engagement protrusion 47. The illustrated engagement portion 37 is a through hole. However, the engagement portion can also be a recess. The lid 3B, in a state in which the insertion tube 40 is inserted into the opening 30, is connected in place by engaging the engagement protrusion 47 to the engagement portion 37. In the interior casing, however, it is also possible that an engagement protrusion is provided on the inner surface of the opening of the major body portion, that an engagement portion for engaging the engagement protrusion to be engaged with is provided around the peripheral surface of the insertion tube of the lid, and that the lid is detachably connected to the major body portion.

Further, the illustrated interior casing 3 includes a positioning mechanism in order to prevent the insertion tube 40 from being inserted into the major body portion 3A in a wrong direction. The illustrated positioning mechanism includes a positioning ridge 38 provided on the inner surface of the opening end of the major body portion 3A, and a guide groove 48 provided on the insertion tube 40 of the lid 3B. The positioning ridge 38 and the guide groove 48 are provided in extension toward the insertion direction of the lid 3B. Regarding the lid 3B, while the positioning ridge 38 is guided to the guide groove 48, the insertion tube 40 is inserted into the opening 30 of the major body portion 3A and connected to the major body portion 3A in an accurate posture. However, the positioning mechanism can also include a positioning ridge provided on the insertion tube of the lid, and a guide groove provided on the inner surface of the opening end of the major body portion. Further, the positioning mechanism of the interior casing does not necessarily have to be composed of the positioning ridge and the guide groove, because such wrong insertion of the lid can be prevented by arranging an asymmetrical shape for the outer contour of the insertion tube of the lid and the inner contour of the opening end of the major body portion where the insertion tube is to be inserted.

In the above-described interior casing 3, when the battery 1 is loaded in the storage portion 5 of the major body portion 3A and when the lid 3B is mounted to the opening 30 of the major body portion 3A, the battery 1 is accommodated in a given position of the interior casing 3. In the pocketable body warmer with such structure, the opening 30 of the major body portion 3A is opened by removing the lid 3B of the interior casing 3, so that the battery 1 is loaded in and unloaded from the opening 30 to easily replace the battery 1. Because of this arrangement, regardless of residual capacity of the battery 1 loaded inside, the pocketable body warmer can be continuously used when a spare battery is prepared in advance. Further, in the interior casing 3, when the opening 30 of the major body portion 3A is closed by the lid 3B, the opposite electrodes of the battery 1 are pressed from both sides between the lid-side contact point 12 disposed on the end plate 43 of the lid 3B and the case-side contact point 11 disposed on the bottom plate 31 of the major body portion 3A in order to achieve an electrical connection of the battery 1 to the contact points. That is to say, since the electrical connection is established by allowing the electrodes of the battery 1 to be in direct contact with the case-side contact point 11 and the lid-side contact point 12, reliability can be increased while the cost of manufacture is reduced by omitting unnecessary contact points. In particular, since the electrical contact between the electrode and the contact point is designed to be established by closing the opening 30 of the interior casing 3 by the lid 3B to press the opposite ends of the electrode of the battery 1 loaded inside, the electrical contact can be maintained securely in mechanical terms as well, resulting in increased reliability that much.

Further, as shown in FIG. 3, the lid 3B includes, in its top plate 41A being the operation surface of the pocketable body warmer, a connection terminal 15 to be connected with an external apparatus, an operation unit 16 for switching on/off the pocketable body warmer, and a display 17 for indicating residual capacity and abnormal state of the battery.

Battery

The battery 1 is loaded in the storage portion 5 of the interior casing 3. The illustrated battery 1 is a cylindrical AA size battery 1. The battery 1 to be used can be either a secondary battery or a primary battery. Thus, in the pocketable body warmer where a battery with the same specification as that of a commercially available primary battery can be loaded, when a battery becomes short of capacity after use for a long period of time and when a spare secondary battery is not available at hand, the battery can be replaced with a commercially available primary battery. Although an AA size battery is loaded in the illustrated pocketable body warmer, another type of battery including a D size battery, a C size battery, or even a square-shaped battery can be loaded in the pocketable body warmer. A secondary battery to be used includes, for example, a nickel-hydrogen battery and a nickel-cadmium battery.

Further, the pocketable body warmer loaded with a secondary battery can also incorporate a battery recharging circuit. Such pocketable body warmer is provided with a connection terminal for a recharging operation, and the secondary battery loaded inside is charged by connecting via the connection terminal to an external apparatus such as a battery charger. The illustrated pocketable body warmer is provided with the connection terminal 15 on the top plate 41A of the lid 3B. The connection terminal 15 is a USB terminal 15A for connecting with a USB cable. In the pocketable body warmer, the USB cable is connected to the USB terminal 15A so that the loaded battery 1 can be recharged by the use of a personal computer or the like. Further, communication information can also be inputted from a personal computer for changing a using environment, a configuration, etc. of the pocketable body warmer.

Since the pocketable body warmer is detachably loaded with the battery 1, the body warmer itself does not necessarily have to have a circuit for charging the battery 1. For example, the battery 1 loaded in the pocketable body warmer can be replaced by charging by an external battery charger. Thus, with a simplified structure of the pocketable body warmer, the battery 1 can be ideally recharged. In particular, a recharged battery is prone to be heated by a charging operation, and the heat is very high especially at the last period of charging operation. Such an increased temperature leads to degradation of the battery. When the battery is recharged by an external battery charger instead of charging the battery inside the pocketable body warmer, the pocketable body warmer is not filled with the heat caused by charging the battery, in other words, a temperature increase of the loaded battery is reduced to minimum, and the degradation of the battery caused by a temperature increase can be effectively avoided.

Heater

The heater 4 is disposed between the metallic exterior casing 2 and the interior casing 3 and is thermally connected to the metallic external casing 2. The heater 4, in an electrified state, heats the metallic exterior casing 2. The heater 4 can be a heating sheet. The heating sheet used in the illustrated pocketable body warmer is a planar PTC element. The planar heater 4 being the PTC element, in a posture opposing the inner surface of the metallic exterior casing 2, is disposed proximately to the metallic exterior casing 2 in a thermally connected state. Since the heater 4 can be thermally connected to the inner surface of the metallic exterior casing 2 over a wide area, the heat generated by the heater 4 can be efficiently conducted to the metallic exterior casing 2. However, the heater does not necessarily have to be a heating sheet. A heater shaped other than a sheet can be efficiently thermally connected to the metallic exterior casing via a thermally coupling resin or the like.

Further, when the heater 4 being the PTC element rises up to a predetermined temperature after electrification, the electric resistance rapidly increases and the current is substantially shut down. Therefore, since the heater 4 being the PTC element has a function of self-controlling the temperature to be below a predetermined temperature, the maximal temperature can be made below a predetermined temperature without using a control circuit for controlling the temperature. In addition, the heater being the PTC element can also control the temperature by controlling the current flow during electrification. Furthermore, besides the planar PTC element, the heater to be used may include a transistor and a resistive substance for heat generation.

In the pocketable body warmer shown in FIG. 3, FIG. 5, FIG. 6, FIG. 10 and FIG. 11, the planar heater 4 is disposed in the bottom of the metallic exterior casing 2. The heater 4 is disposed on the inner side of the bottom plate 2B of the metallic exterior casing 2. The heater 4 disposed between the metallic exterior casing 2 and the interior casing 3 is disposed in a given place of the metallic exterior casing 2 via the interior casing 3 connected to the metallic exterior casing 2, and is disposed to the metallic exterior casing 2 in a thermally connected state. Further, in the illustrated pocketable body warmer, a holder plate 6 is disposed between the interior casing 3 and the heater 4 to hold the heater 4 in place. In the pocketable body warmer, the heater 4 is interposed between the holder plate 6 and the inner surface of the metallic exterior casing 2 to hold the heater 4 in place, and is thermally connected to the metallic exterior casing 2. The illustrated interior casing 3 has the holder plate 6 fixed to the surface of the bottom plate 31, and the heater 4 is connected to the surface of the holder plate 6. Further, the bottom plate 31, with the heater 4 being disposed on the surface of bottom plate, is fixed to the bottom plate 2B of the metallic exterior casing 2 by the set screw 21, and the heater 4 is disposed in place on the inner side of the bottom plate 2B.

Further, the holder plate 6 also serves to restrain thermal conduction from the heater 4 to the interior casing 3. The holder plate 6 shown in FIG. 3 has the heater 4 disposed on the front surface, and the back surface is disposed in a posture opposing the bottom plate 31 of the interior casing 3. The holder plate 6 is made of a plastic material having low thermal conductivity, and the heat generated by the heater 4 is restrained from conduction to the interior casing 3. Further, a gap 60 is defined between the holder plate 6 and the interior casing 3, with the heat generated by the heater 4 being prevented from being directly conducted to the bottom plate 31 of the interior casing 3. The interior casing 3 shown in FIG. 3, FIG. 6 and FIG. 11 respectively has an integrally formed fixture boss 39, in protrusion from the surface, disposed on the opposite sides of the bottom plate 31 in order to define the gap 60 between the bottom plate 31 and the holder plate 6. The holder plate 6 is provided with a through hole 62 for inserting the set screw 61. By thread-screwing the set screw 61, which extends through the through hole 62, into the fixture boss 36 of the bottom plate 31, the gaps 60 are defined at predetermined intervals between the holder plate 6 and the bottom plate 31, and the holder plate 6 is fixed to the interior casing 3.

In order to dispose the heater 4 in place, the holder plate 6 has the integrally formed positioning rib 63 disposed around the periphery of the heater 4, on a plane where the heater 4 is mounted. Further, the holder plate 6 shown in FIG. 6 is provided with an integrally formed protrusion 64 for wiring in a manner where connection pieces 55A, 56A for metal plates 55, 56 and lead wires 57 connected to the heater 4 will not be in contact with the case-side contact point 11. The protrusion 64 is provided in a state of extending through the bottom plate 31 from the holder plate 6 toward the board storage portion 35. The bottom plate 31, at its center portion, has an opening 31A disposed between the two rows of storage portions 5, and the protrusion 64 of the holder plate 6 is extended through the opening 31A. Further, the protrusion 64 of the holder plate 6, at its center portion, has an integral isolation wall 65 for isolating the connection pieces 55A, 56A of the metal plates 55, 56 connected to the both sides of the heater 4.

The planar heater 4 is the substantially disk-shaped PTC element 4A, on both sides of which is formed a silver-plated electrode respectively. The heater 4 supplies electric power, with the metal plates 55, 56 being pressed to the electrode surfaces on both sides. The metal plate 55, on the inner surface of the heater 4, which is disposed on the surface of the holder plate 6, includes a connection piece 55A protruding toward the periphery, and is connected to the circuit board 7 via the lead wires 57 connected to the connection piece 55A. Further, the metal plate 55 is provided with a plurality of elastic pieces 55B protruding toward the periphery. Under the effect of elastic force of the elastic piece 55B, the heater 4 is pressed outwardly to allow the both sides of the heater 4 to be in secure contact with the metal plates 55, 56 and also to allow the heater 4 to be securely in thermal contact with the bottom plate 2B of the metallic exterior casing 2. The metal plate 56, at the outward face of the heater 4, disposed on the inner surface of the bottom plate 2B of the metallic exterior casing 2 is provided with a connection piece 56A protruding toward the periphery, and is connected to the circuit board 7 via the lead wire 57 connected to the connection piece 56A. Further, the metal plate 56 is provided with a connection piece 56B protruding toward the both sides, with the metal plate 56 being connected to the holder plate 6, so as not to come out loosely, by connecting the elastic piece 56B to the holder plate 6. The illustrated holder plate 6 is provided with an insertion portion 66, positioned on opposite sides, to be engaged by inserting the tip of the connection pieces 56B. The heater 4, in a state of being interposed between the metal plate 55 and the metal plate 56, is disposed inside the positioning rib 23 of the holder plate 6, and is maintained in place by inserting, into the insertion portions 66 of the holder plate 6, the tip of the connection pieces 56B protruding on opposite sides of the metal plate 56. In a state where the heater 4 is connected to the surface of the holder plate 6 fixed to the bottom plate 31 of the interior casing 3, the interior casing 3 is inserted into the metallic exterior casing 2, the interior casing 3 is fixed to the metallic exterior casing 2, and the heater 4 is fixed, in a thermally connected state, to a given place of the metallic exterior casing 2. The heat generated by the heater 4 is efficiently conducted to the bottom plate 2B of the metallic exterior casing 2 via the metal plate 56. Further, application of thermal coupling paste such as silicone paste on the metal plate 56 can also increase thermal conduction efficiency of the metallic exterior casing 2 with respect to the bottom plate 2B.

As described above, the heater 4 being the planar PTC element 4A is disposed in a thermally connected state with the inner surface of the bottom plate 2B of the metallic exterior casing 2 being in a posture parallel to the bottom plate 2B. The pocketable body warmer thus structured can efficiently conduct the heat generated by the planar PTC element 4A to the entirety of the tube 2A via the bottom plate 2B. The heater 4 thermally connected to the bottom plate 2B of the metallic exterior casing 2, as indicated by arrow in FIG. 10, conducts the generated heat to the bottom plate 2B, further conducts the heat from the bottom plate 2B to the tube 2A, and heats the entire surface of the metallic exterior casing 2. It is, therefore, advantageous that a single piece of heater 4 is disposed at the bottom of the metallic exterior casing 2 so that the entire surface of the metallic exterior casing 2 can be heated effectively and uniformly. The heater 4 is set to heat the metallic exterior casing 2, for example, between 42° C. and 46° C.

The illustrated pocketable body warmer incorporates a single piece of heater 4, but can also incorporate a plurality of heaters. A pocketable body warmer incorporating a plurality of heaters can set each individual heater either at the same predetermined temperature or at different temperatures. A pocketable body warmer incorporating heaters with different predetermined temperatures can control the temperature of the metallic exterior casing by switching the electrified heaters. For example, when a pocketable body warmer incorporates two pieces of heaters, one of the heaters is set at a predetermined temperature of 45° C. and the other of the heaters is set at a predetermined temperature of 48° C. In such pocketable body warmer, the heater with the predetermined temperature of 45° C. is electrified to heat the metallic exterior casing up to 45° C. Likewise, the heater with the predetermined temperature of 48° C. is electrified to heat the heater up to 48° C. Furthermore, when both heaters are electrified, the metallic exterior casing is subjected to a rapid temperature increase to be heated up to 48° C.

Figure 13:
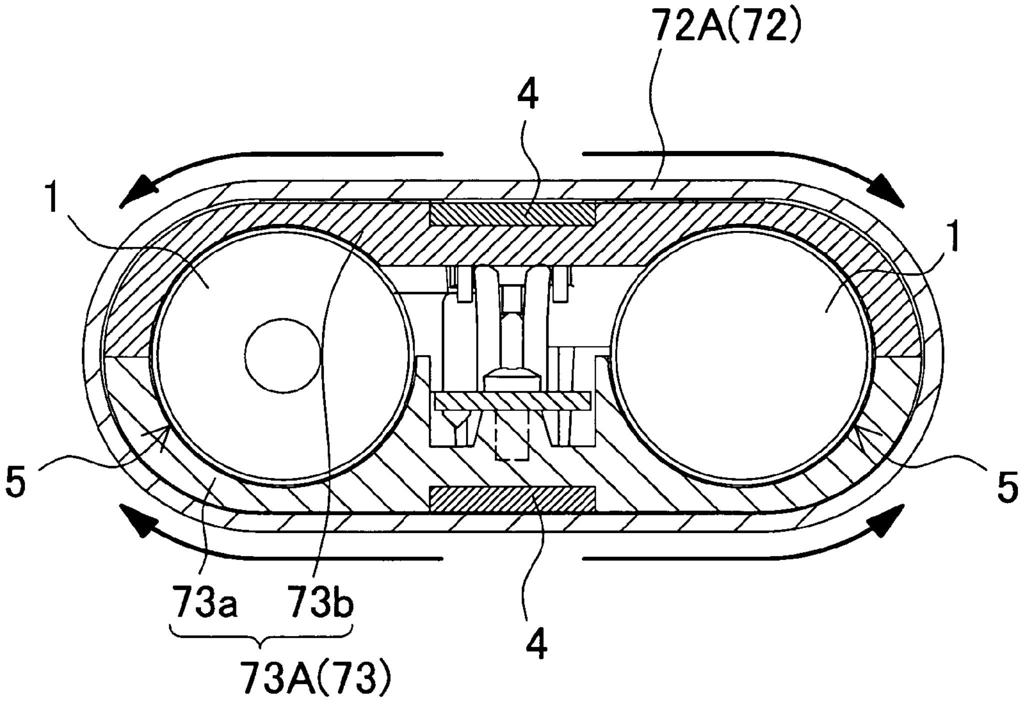
FIG. 13 is a transverse sectional view of the pocketable body warmer in accordance with an alternative embodiment of the present invention.

Further, in the pocketable body warmer shown in FIG. 13, heaters 4 can be disposed on the inner side of the tube 72A of the metallic exterior casing 72. In the illustrated pocketable body warmer, each of the heaters 4 is disposed on the inner side of the opposite surfaces of the tube 72A of the metallic exterior casing 72 so that the entirety of the metallic exterior casing 72 may be heated effectively and uniformly. In the illustrated pocketable body warmer, the heaters 4 disposed on the inner side of the opposite surfaces of the tube 72A are located between the metallic exterior casing 72 and the interior casing 73 and further between two pieces of batteries 1 loaded in the storage portion 5 so that thermal influence on the batteries 1 is reduced. In the pocketable body warmer, the heat generated by the heaters 4 directly heats the tube 72A of the metallic exterior casing 72, and as indicated by arrows, the heat generated by the heaters 4 is conducted to the entirety of the tube 72A to achieve a quick temperature increase.

In the drawing, the major body portion is indicated by 73A, the body casing by 73*a*, and lid casing by 73*b*.

Figure 12:
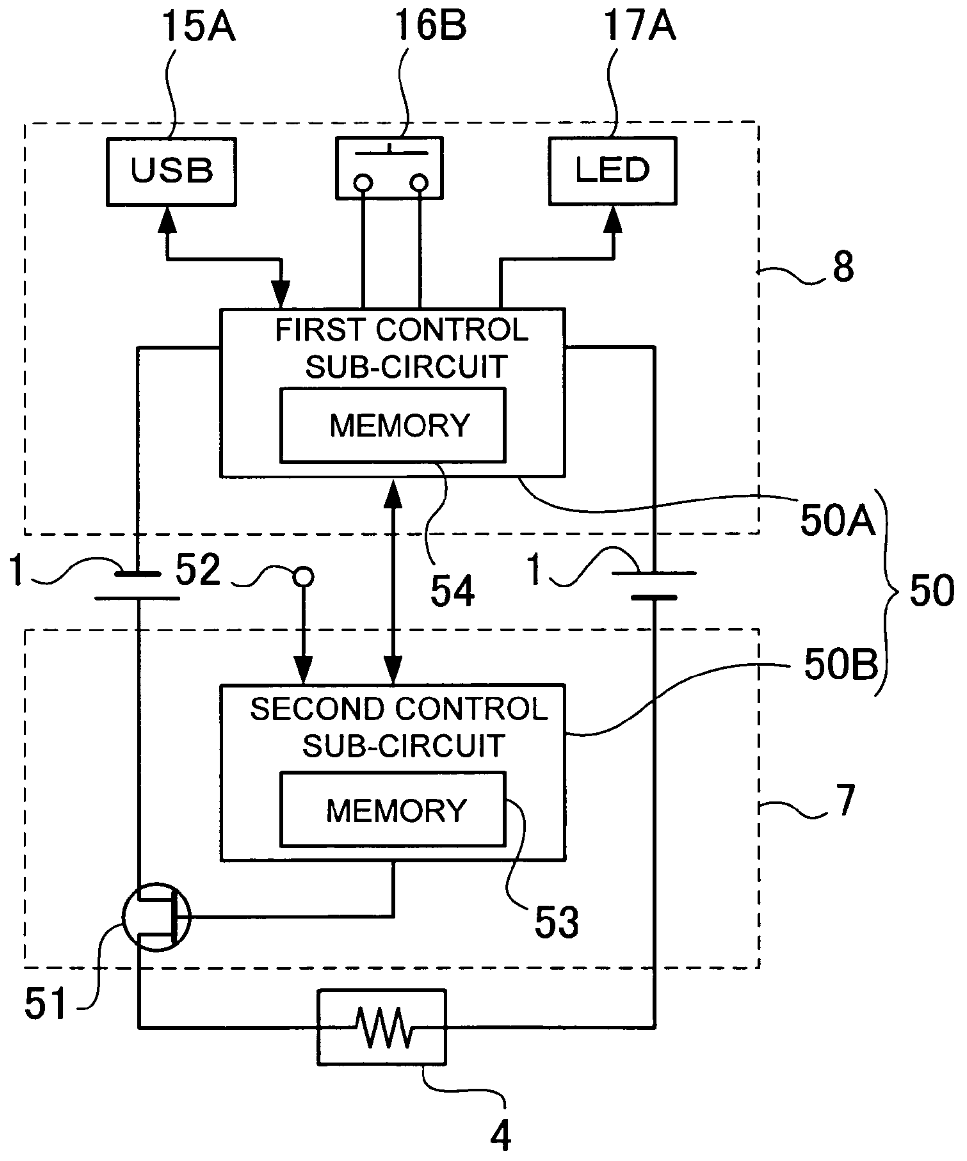
FIG. 12 is a block diagram of the pocketable body warmer in accordance with an embodiment of the present invention.

FIG. 12 is a block diagram of the pocketable body warmer. The pocketable body warmer shown in the diagram includes a switching element 51 connected between the battery 1 and the heater 4, a control circuit 50 for controlling the electric power supplied from the battery 1 to the heater 4 by controlling the switching element 51 to be switched on/off, and a temperature sensor 52 for detecting the temperature surrounding the battery. In the pocketable body warmer, since the heater 4 being the PTC 4A is series-connected to the battery 1 via the switching element 51, the heater 4 also serves as a protection circuit for the battery 1. For example, even if the switching element is internally short-circuited or welded to result in maintaining an ON state, the electric resistance becomes rapidly high when the heater 4 being the PTC 4A reaches the predetermined temperature, whereby the electric current is substantially shut down to protect the battery 1.

The control circuit 50 controls the power supplied to the heater 4, and thus controls the temperature of the heater 4, that is, the surface temperature of the metallic exterior casing 2. The control circuit 50 includes a first control sub-circuit 50A mounted to the circuit board 8 incorporated in the lid 3B of the interior casing 3, and a second control sub-circuit 50B mounted to the circuit board 7 incorporated in the major body portion 3A. The first control sub-circuit 50A mounted to the circuit board 8 and the second control sub-circuit 50B mounted to the circuit board 7 are connected together via the pin jack 13 and the pin terminal 14.

The second control sub-circuit 50B controls the duty of switching on/off the switching element 51 in a predetermined cycle to control the temperature of the metallic exterior casing 2. When the period of time is made longer for the second control sub-circuit 50B to keep the switching element 51 in an ON state, the temperature of the heater 4 can be made high, that is, the temperature of the metallic exterior casing 2 can be made high. Conversely, when the period of time is made shorter for the second control sub-circuit to keep the switching element 51 in an ON state, the temperatures of the heater 4 and the metallic exterior casing 2 can be made low. Further, the second control sub-circuit 50B can also control the duty of the switching element 51 by receiving a signal from the temperature sensor 52 detecting the temperature surrounding the battery 1, whereby the heater 4 and the metallic exterior casing 2 can be maintained at a predetermined temperature.

The second control sub-circuit 50B incorporates a memory 53 for storing a state of predetermined temperature. The second control sub-circuit 50B controls the duty of switching on/off the switching element 51 to obtain the state of the predetermined temperature stored in the memory 53. The second control sub-circuit 50B does not necessarily have to control the temperature on the basis of the duty of switching on/off the switching element 51 in a predetermined cycle. The second control sub-circuit 50B can also maintain the predetermined temperature for the heater 4 on the basis of the signal received from the temperature sensor 52, where when the temperature of the heater 4 becomes higher than predetermined, the switching element 51 is switched off, and when the temperature of the heater 4 becomes lower than predetermined, the switching element 51 is switched on. The pocketable body warmer shown in FIG. 6 and FIG. 10 respectively has the temperature sensor 52 at the back of the heater 4 so that the temperature of the heater 4 can be quickly detected. The temperature sensor 52 is connected to the circuit board 7.

The memory 53 in the second control sub-circuit 50B stores the states of the predetermined initial temperature and the predetermined normal temperature. The predetermined initial temperature is set to be higher than the predetermined normal temperature. In the second control sub-circuit, the heater 4 is heated up to the predetermined initial temperature at an initial stage of switching on the power switch 16B of the pocketable body warmer, followed by controlling the heater to be maintained at the predetermined normal temperature. In this way, the pocketable body warmer, where the heater 4 heats the metallic exterior casing 2, heats up quickly in a short period of time in order to warm a cooled user. Subsequently, the body warmer turns to the predetermined normal temperature so as to be used for a longer period of time with a reduced average current of the heater 4.

Further, in order to detect the state of being unused, an ambient temperature sensor can also be disposed in the pocketable body warmer. Although not shown, the ambient temperature sensor is disposed, for example, in the lid. This ambient temperature sensor can detect the ambient temperature, for example, by being provided with an aperture to the lid to introduce the open air through the aperture. The pocketable body warmer is designed to judge the state that the body warmer is not used, on the basis of the detected temperature which is the ambient temperature detected by the ambient temperature sensor, that is, the state of non-use, and switch off the switching element.

The first control sub-circuit 50A, being connected to the battery 1 loaded in the major body portion 3A in a state that the lid 3B of the interior casing 3 is connected to the major body portion 3A, controls various functions installed in the lid 3B. The pocketable body warmer shown in FIG. 3 and FIG. 12 respectively includes, on the top plate 41A of the lid 3B, a connection terminal 15 to be connected to an external apparatus, an operation unit 16 for operating the body warmer to be switched on/off, and a display 17 for indicating residual capacity and abnormal state of the battery 1. Therefore, the first control sub-circuit 50A has electronic components installed for controlling such functions.

The pocketable body warmer shown in FIG. 3 and FIG. 12 respectively has a connection terminal 15 connected to the first control sub-circuit 50A. The connection terminal 15 is a USB terminal 15A, which is provided on the operation board of the lid 3B. The illustrated pocketable body warmer has a cap 18 mounted to protect the connection terminal 15. The USB terminal 15A is connected via the USB cable to a computer. The first control sub-circuit 50A, being connected to the computer via the USB terminal 15A, is designed to change a state of predetermined temperature stored in memory 53, based on a control signal inputted from the computer. The pocketable body warmer, being connected to the computer, can be adjusted by a user to predetermine his or her optimal temperature. Further, the pocketable body warmer can also charge the incorporated battery 1 by the electric power supplied via the USB terminal 15A. The pocketable body warmer realizing such functions can be provided with a charging circuit in the first control sub-circuit.

The operation unit 16 for switching on/off the pocketable body warmer includes a power switch 16B and a press button 16A provided atop of the power switch 16B. The power switch 16 is an ON/OFF switch, where a plunger is manipulated through the press button 16A to switch the pocketable body warmer into an ON state and an OFF state.

Figure 10:
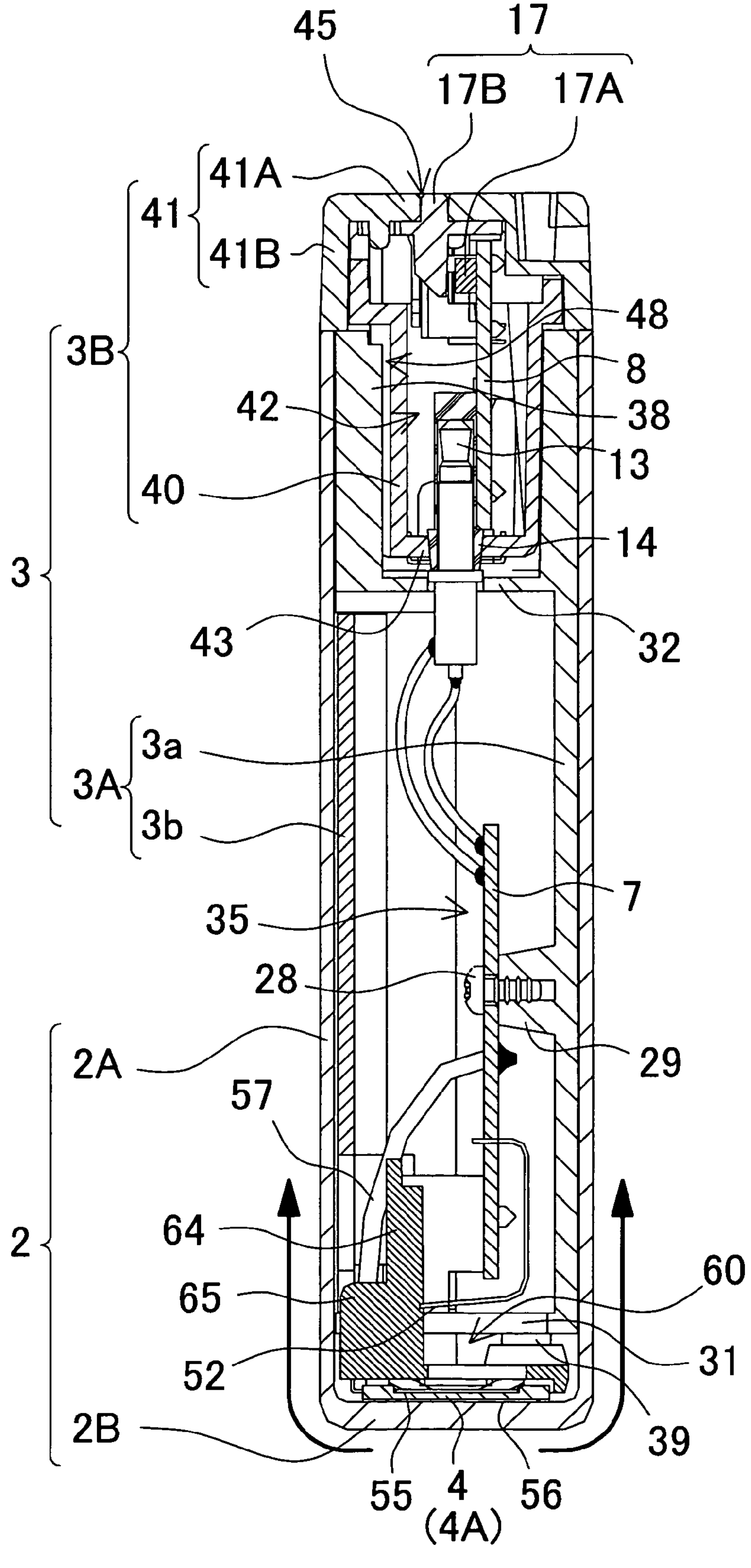
FIG. 10 is a cross-sectional view, taken along line B-B, of the pocketable body warmer shown in FIG. 3.
Figure 11:
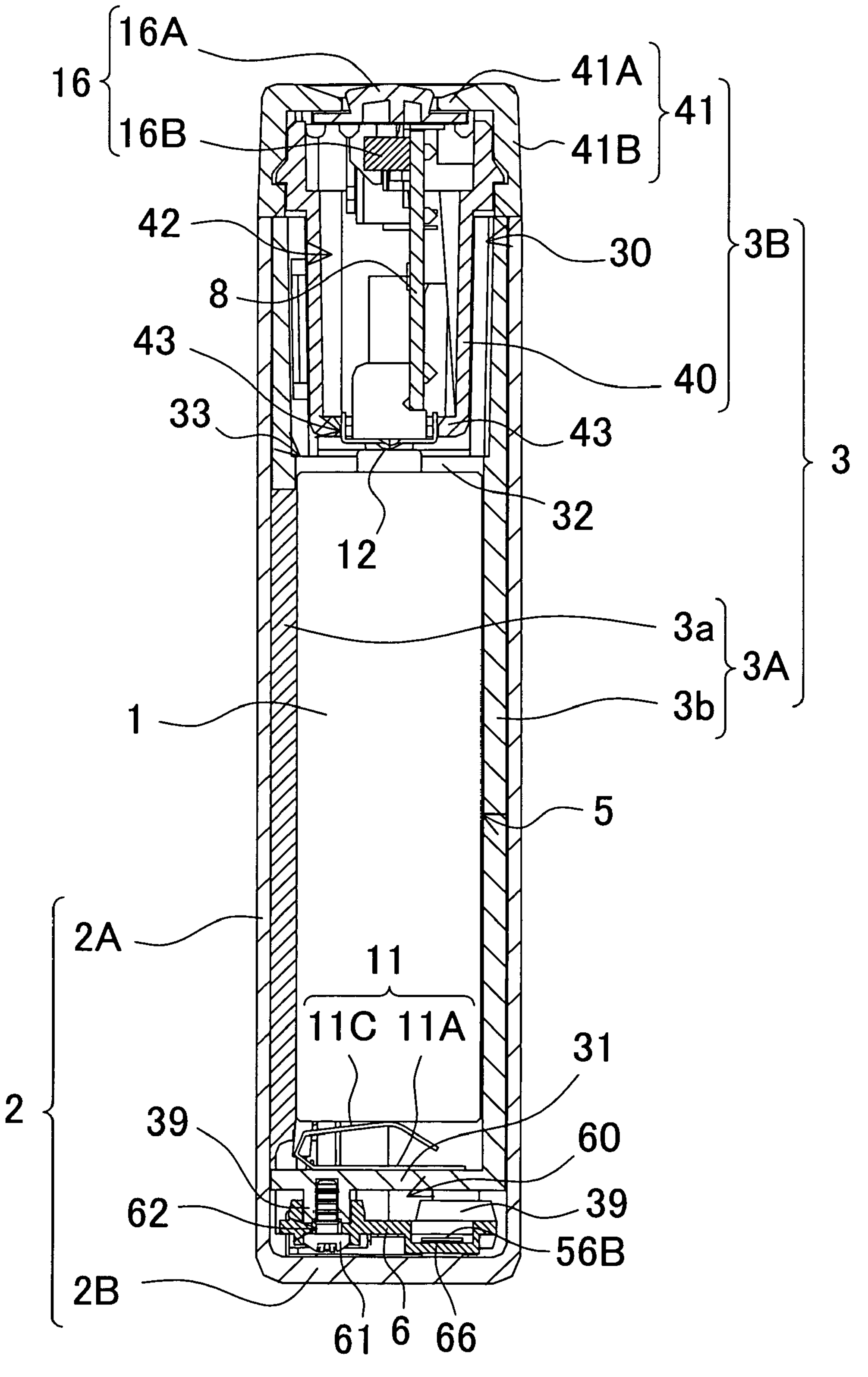
FIG. 11 is a cross-sectional view, taken along line C-C, of the pocketable body warmer shown in FIG. 3.

Further, the pocketable body warmer shown in FIG. 3, FIG. 10 and FIG. 12 respectively is provided, on the top plate 41A of the lid 3B, with the display 17 for indicating residual capacity of the battery 1 and the state of the pocketable body warmer being used. The display 17 includes an LED 17A fixed to the circuit board 8 and a lighting guide 17B for transmitting the lighting of the LED 17A to the outside of the lid 3B. The LED 17A, being fixed to the circuit board 8 incorporated in the lid 3B, has its blinking state controlled by the first control sub-circuit 50A. The lighting guide 17B, being a product such as translucent plastic material and glass, is disposed at a display aperture 45 provided on the operation surface of the lid 3B, and the light emitted by the LED 17A is guided to the outside of the lid 3B for display. However, either the lid can directly expose the LED from the display aperture to the outside for display, or the lid in entirety or in part can be made of a translucent plastic material to permeate the LED emission for outside display.

The display 17, being controlled by the first control sub-circuit 50A, indicates a state of battery consumption or temperature or an abnormal state of the battery 1 by means of lighting state of the LED 17A, for example, by a change in emitted color or blinking state. As such, the pocketable body warmer capable of indicating the state of the battery carries the advantage that a battery replacement timing and abnormal temperature can be quickly detected. In the first control sub-circuit 50A, the lighting pattern for lighting the LED 17A is stored in a memory 54. The lighting pattern of the LED 17A stored in the memory 54 of the first control sub-circuit 50A is altered by the computer connected via the USB terminal 15A. In the pocketable body warmer connected to the computer, the lighting state of the LED 17A can be controlled to alter a lighting pattern as may be desired by a user.

In the above-described pocketable body warmer, the circuit board 8 is provided with the first control sub-circuit 50A, while the circuit board 7 is provided with the second control sub-circuit 50B. In the pocketable body warmer, however, the control circuit does not necessarily have to be divided into the first control sub-circuit and the second control sub-circuit; the body warmer can be realized by a control circuit provided on one of the control boards.

Further, FIG. 14 through FIG. 21 represents alternative embodiments of the present invention, respectively showing the pocketable body warmer in which a heater 104 is fixed to the opposite surfaces of the metallic exterior casing 102. In these drawings, however, the structure and configuration having the same functions as shown in the above-described embodiments are suffixed with the same numerals in the last two digits, so that a detailed description shall be omitted.

In a pocketable body warmer shown in FIG. 14 through FIG. 20, a heater 104 is respectively disposed on opposite surfaces of an interior casing 103, and the heater 104 is disposed in a thermally connected state on inner surfaces of a metallic exterior casing 102 (for example, an aluminum material usable in a rough thickness of 0.3 to 1.5 mm, preferably in a thickness of 0.4 to 0.5 mm). The metallic exterior casing 102 is tubular with a closed bottom mating with the interior casing 103. The metallic exterior casing 102 is tubular with planar surfaces 102C on opposite sides being connected to curved surfaces 102D on opposite sides, with the bottom being closed. The metallic exterior casing 102 is heated by the heater 104 disposed in a thermally connected state inside the opposite planar surfaces 102C. In the illustrated pocketable body warmer, the heater 104 composed of a planar PTC element 104A is disposed on the opposite faces of the interior casing 103, and the heater 104 is disposed in a thermally connected state on the inner surfaces of the planar surfaces 102C of the metallic exterior casing 102.

Figure 14:
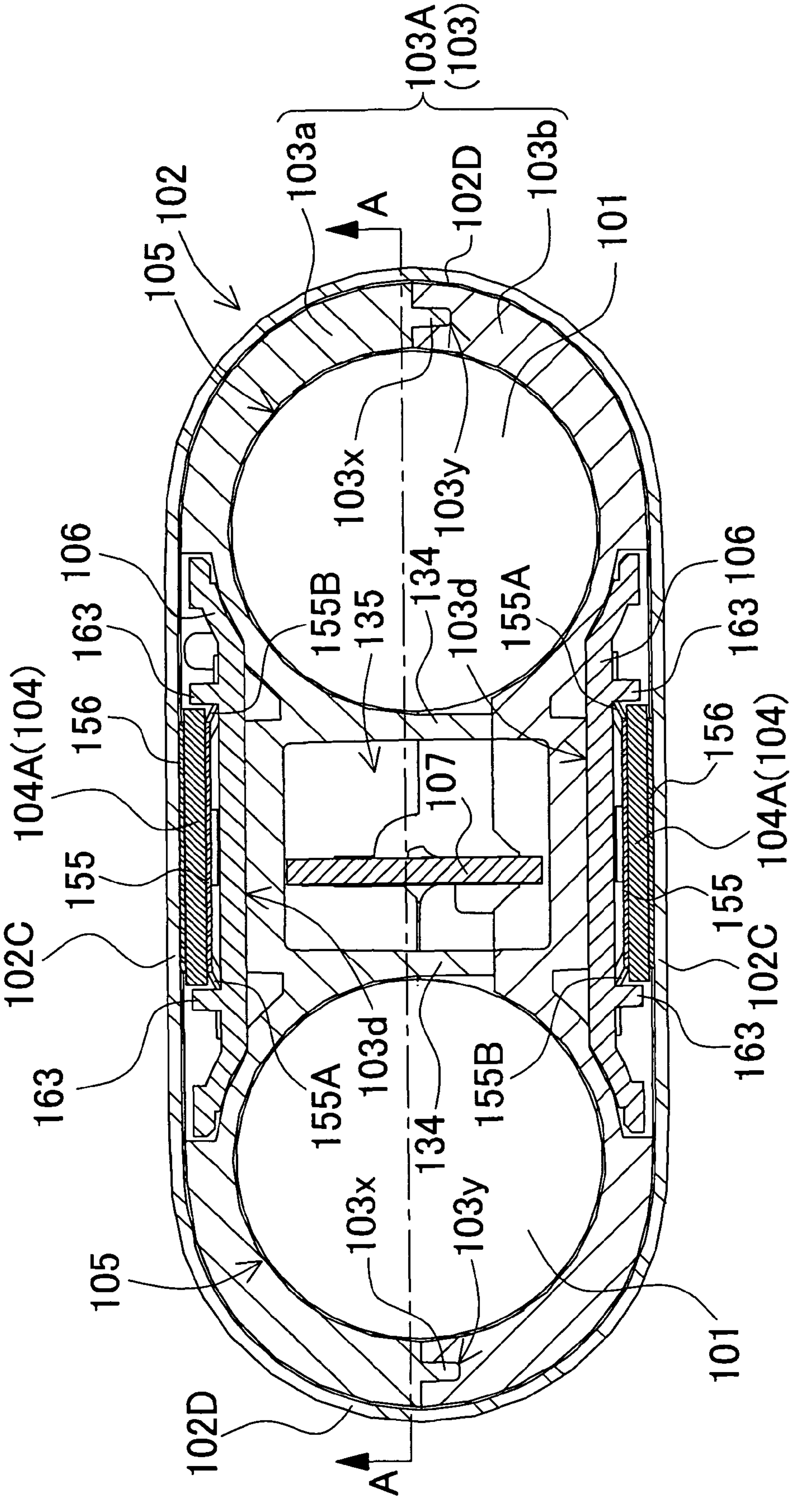
FIG. 14 is a transverse sectional view of the pocketable body warmer in accordance with another embodiment of the present invention.
Figure 15:
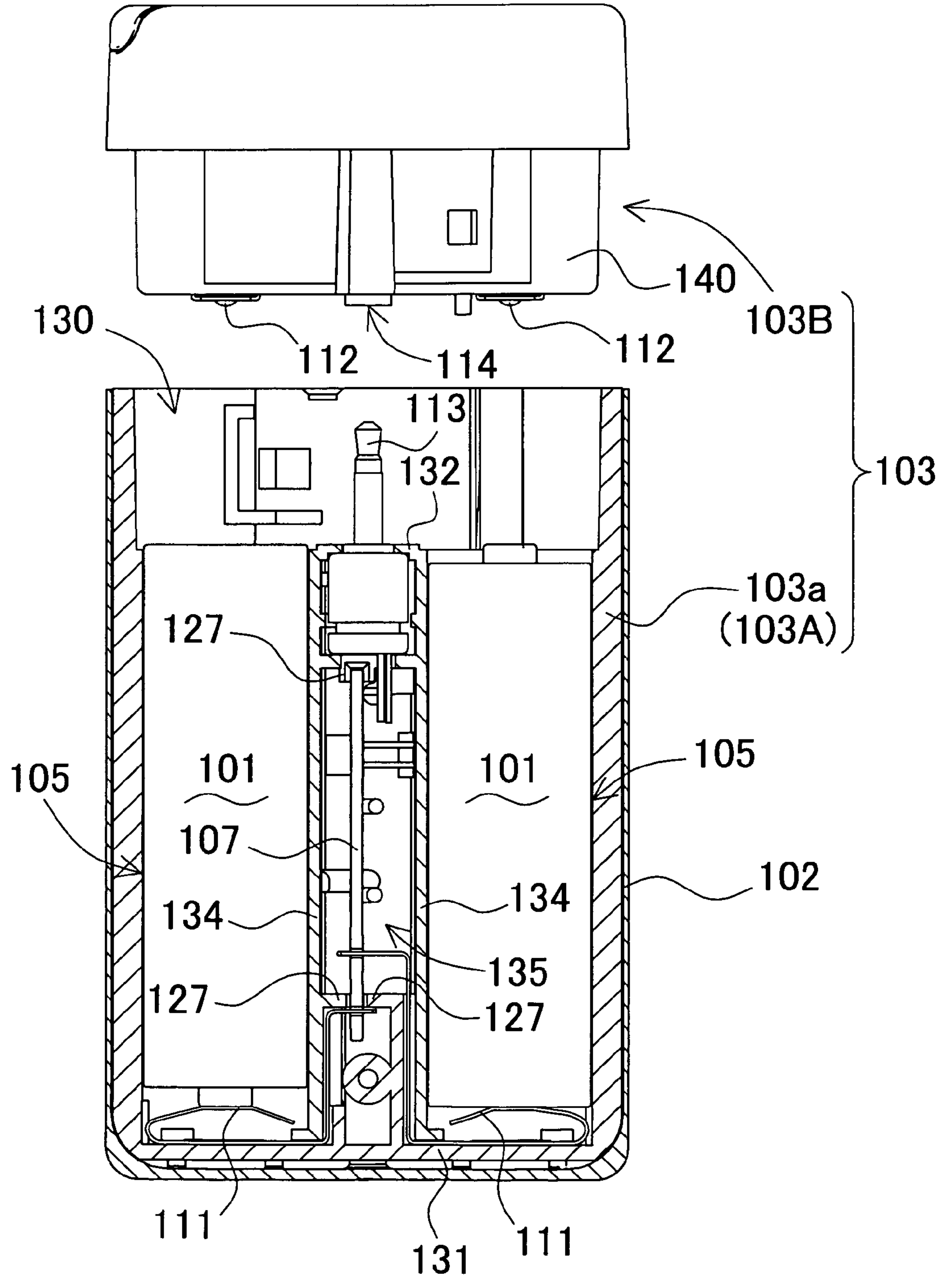
FIG. 15 is an exploded cross-sectional view equivalent to the cross section, taken along line A-A, of the pocketable body warmer shown in FIG. 14.
Figure 16:
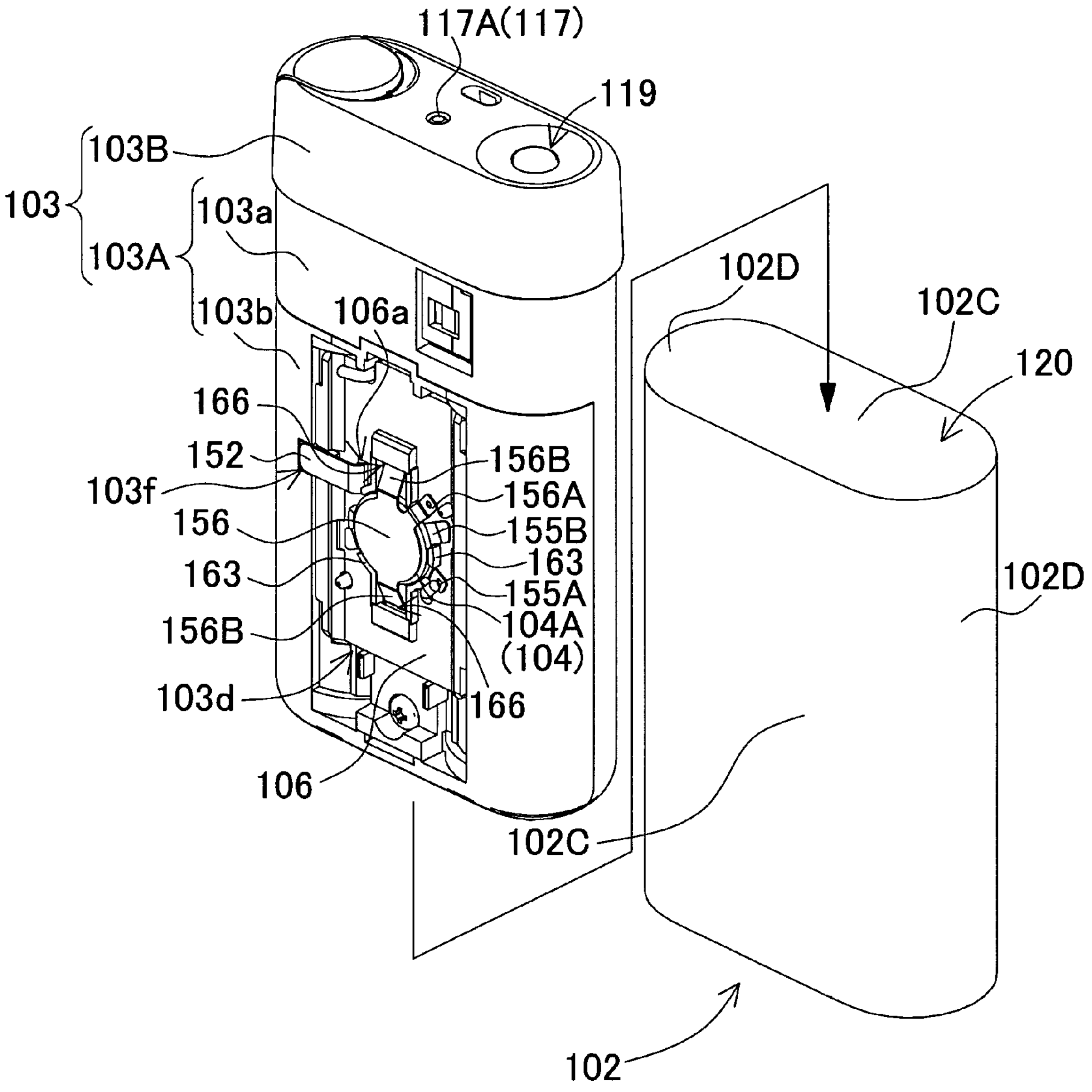
FIG. 16 is an exploded perspective view of the pocketable body warmer in accordance with yet another embodiment of the present invention.
Figure 17:
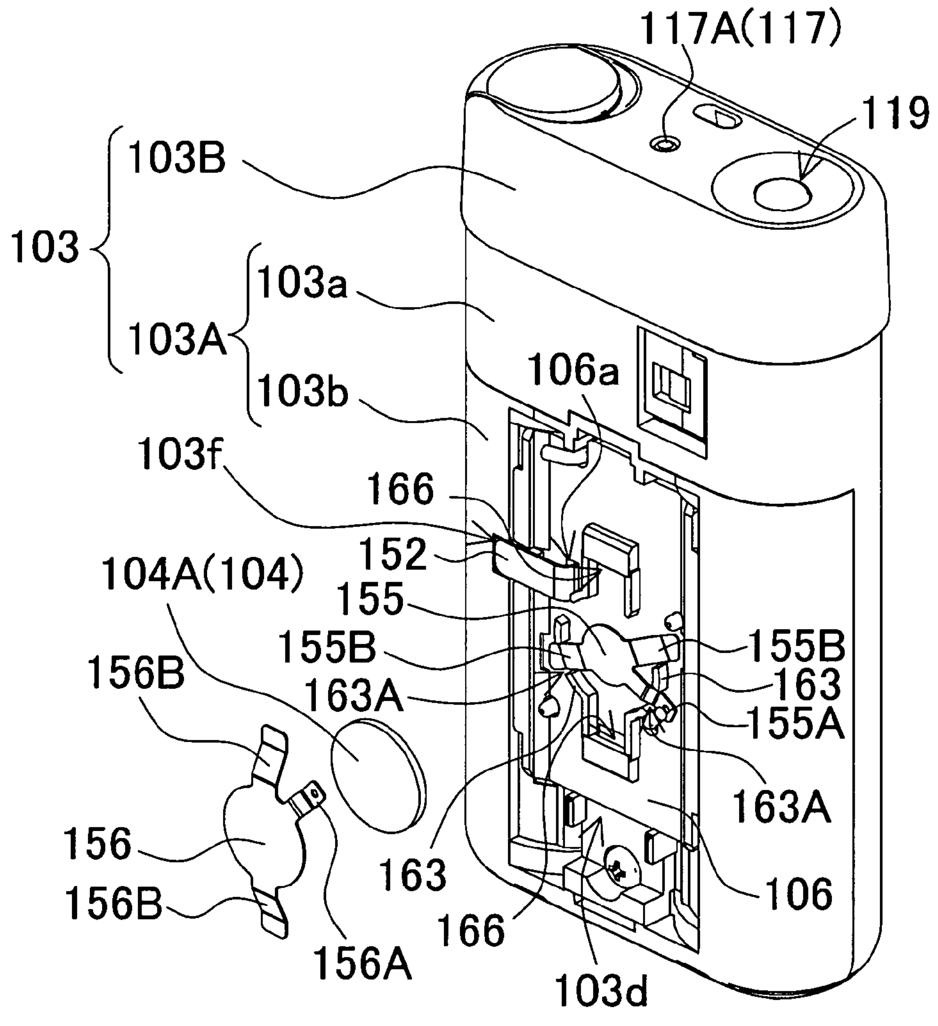
FIG. 17 is an exploded perspective view showing the connection structure of the heater in the pocketable body warmer shown in FIG. 16.
Figure 18:
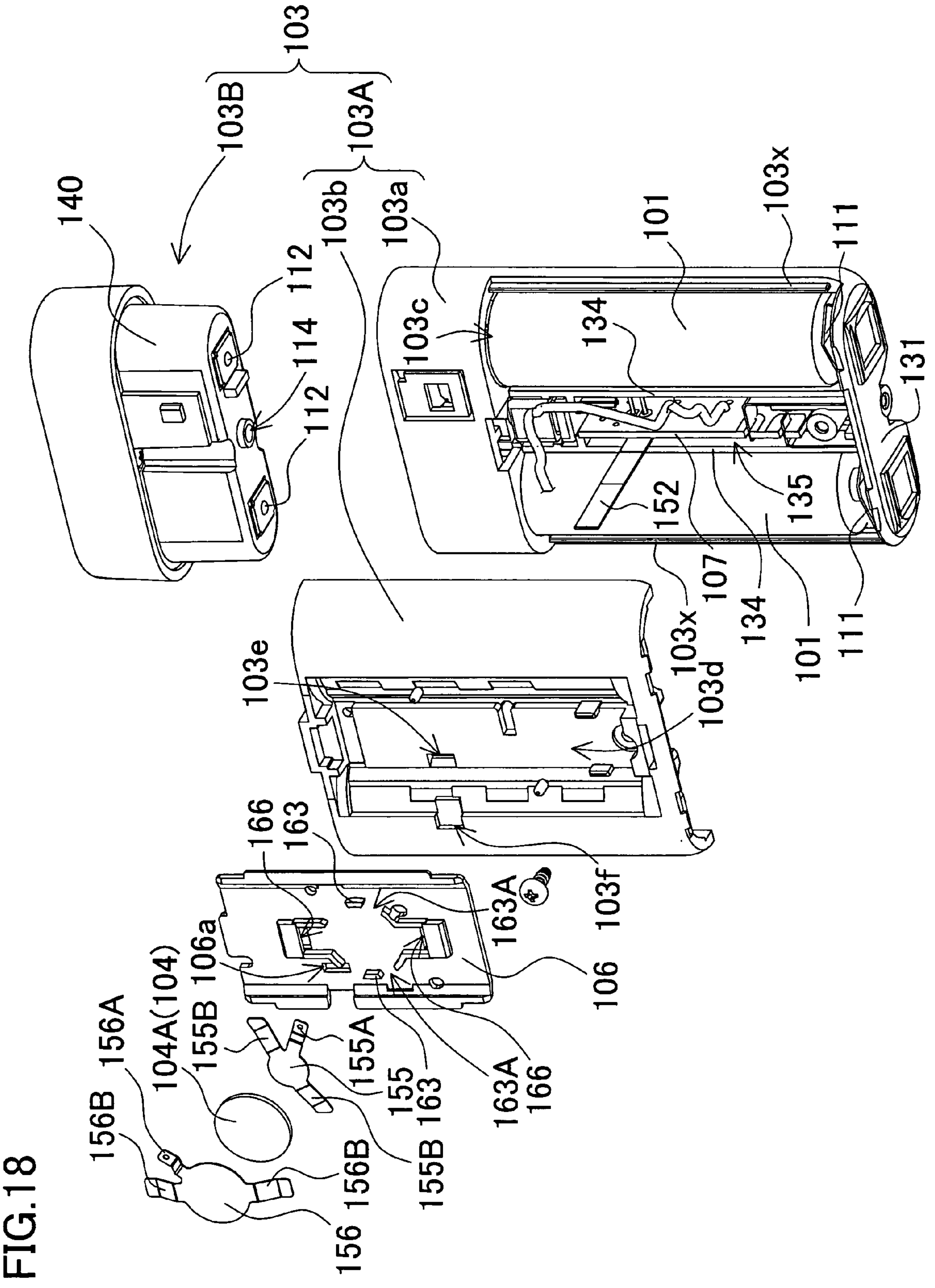
FIG. 18 is an exploded perspective view of the interior casing of the pocketable body warmer shown in FIG. 17.
Figure 19:
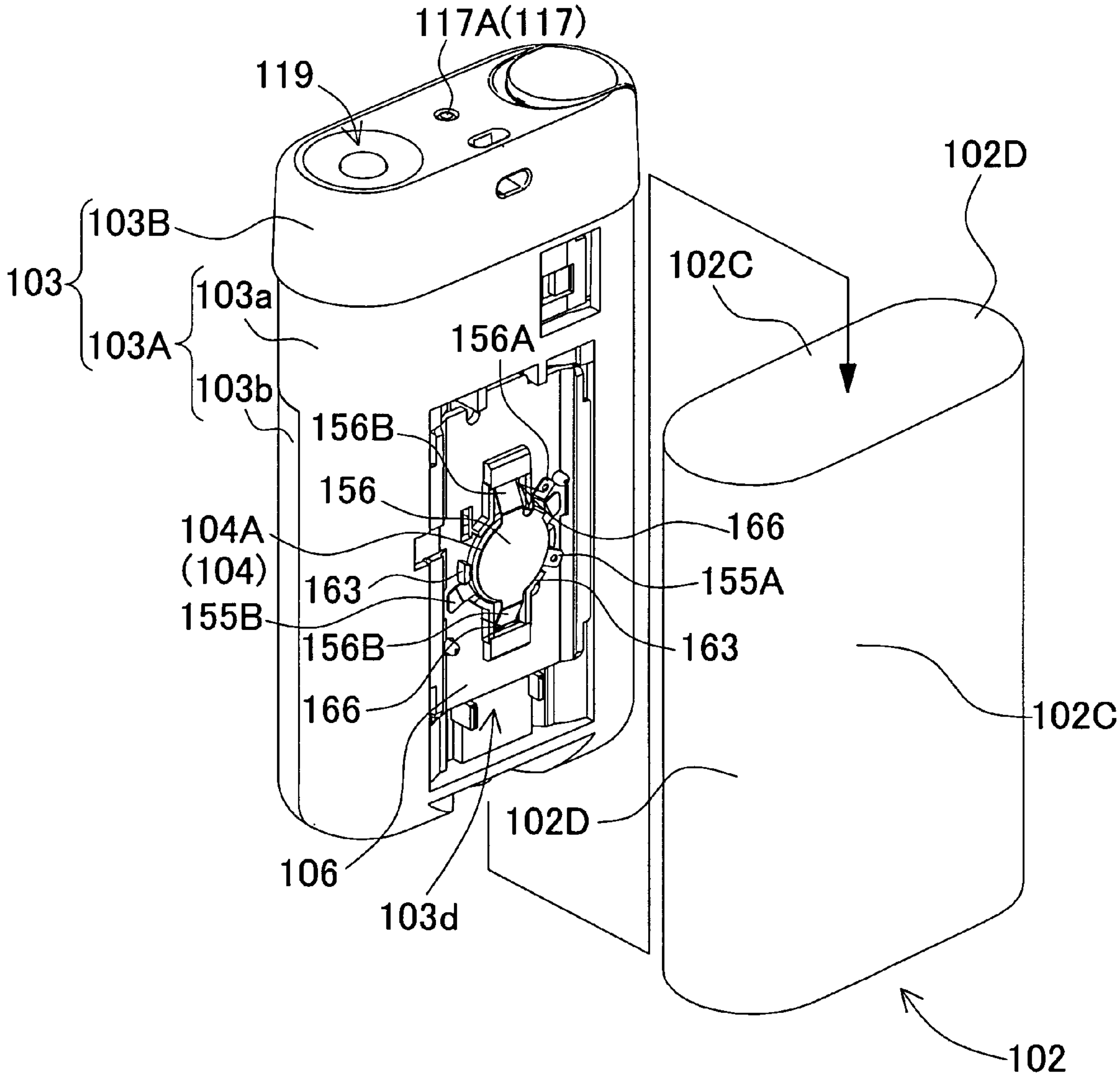
FIG. 19 is a rear perspective view of the pocketable body warmer shown in FIG. 16.
Figure 20:
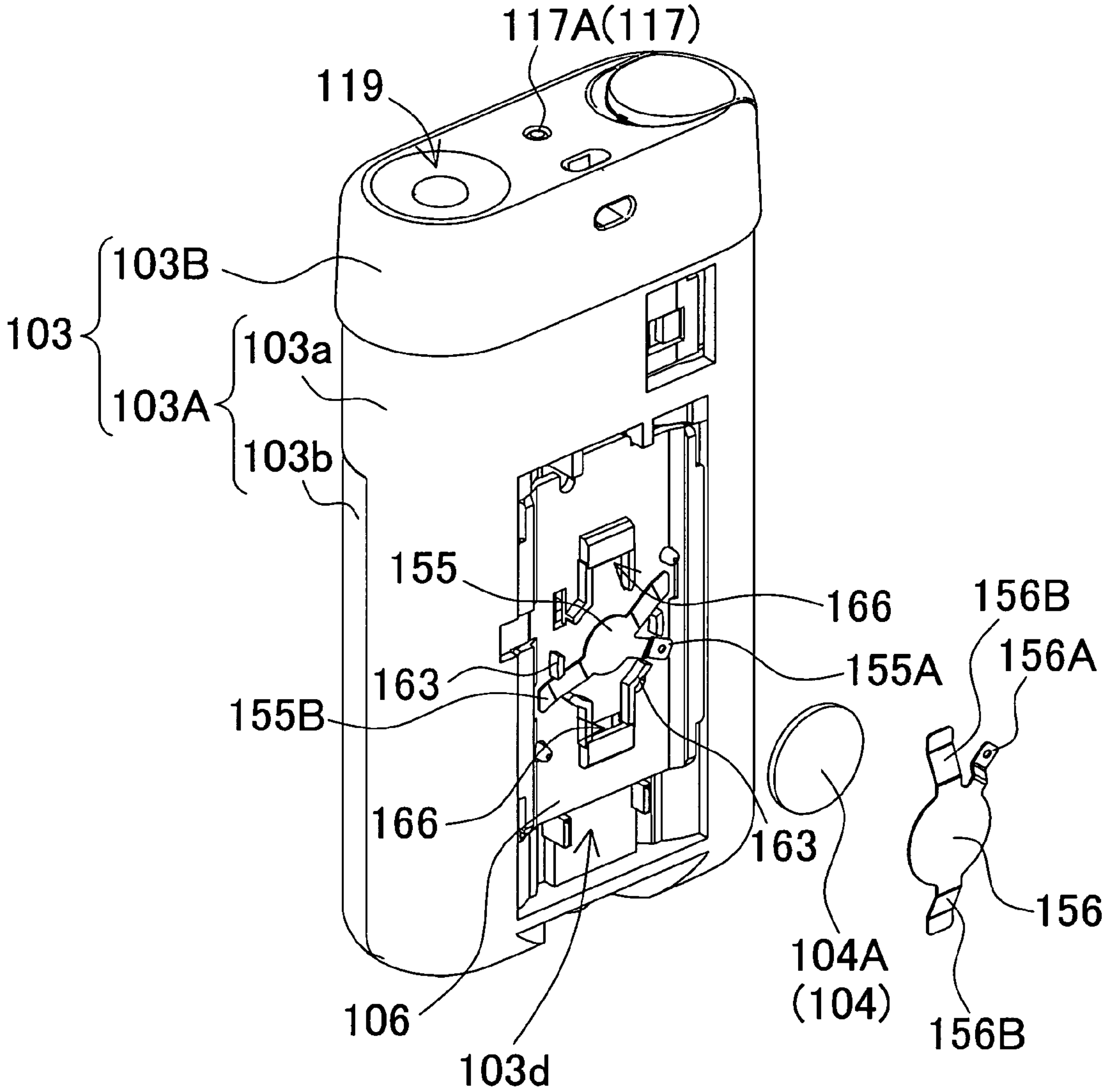
FIG. 20 is an exploded perspective view of the connection structure of the heater in the pocketable body warmer shown in FIG. 19.

The interior casing 103 includes a major body portion 103A loaded with a battery 101, and a lid 103B, detachably connected to an opening 130 of the major body portion 103A, for closing an opening 120 of the metallic exterior casing 102. The major body portion 103A is formed into a tube mating with and along the inner surface of the metallic exterior casing 102, and is provided inside with a storage portion 105 for loading the battery 101 inserted from the opening 130. The illustrated major body portion 103A is provided with two rows of storage portions 105 on the opposite sides of the major body portion 103A, and the storage portions 105 are segmented with two rows of partition walls 134. Further, the major body portion 103A is provided, between the two rows of partition walls 134, with a board storage portion 135 for disposing a circuit board 107 inside. The major body portion 103A as shown in FIG. 14, FIG. 15 and FIG. 18 respectively is provided with the circuit board 107. The circuit board 107 is located between two pieces of batteries 101 loaded in mutually parallel relationship, and is disposed in a posture perpendicular to a plane including the center axes of the two pieces of batteries 101. The circuit board 107 is disposed in place, being supported from opposite sides by support ribs 127 provided in protrusion to the board storage portion 135.

As shown in FIG. 18, in order to dispose the circuit board 107 in the board storage portion 135, the major body portion 103A includes a major body case portion 103*a* shaped with the tubular side face being open, and a lid case portion 103*b* for closing a side opening 103*c* of the major body case portion 103*a*. In the major body portion 103A, the lid case portion 103*b* can be removed from the major body case portion 103*a*, and the side opening 103*c* is opened, which facilitates fixture and wiring of the circuit board 107 with respect to the board storage portion 135. The major body case portion 103*a* and the lid case portion 103*b* are mutually connected by fitting, with a connection groove 103*y*, a ridge 103*x* provided at a tip surface of the peripheral wall on opposite sides.

Further, in the major body portion 103A, a pair of case-side contact points 111 for contacting one of the electrodes of the battery 101 loaded in the storage portion 105 is disposed on the inner surface of a bottom plate 131. The pair of case-side contact points 111 is fixed to the circuit board 107. Further, in the major body portion 103A, as shown in FIG. 15, a pin jack 113 is disposed, in protrusion toward the insertion direction of the insertion tube 140, on an intermediate wall 132 parallel to the opening edge and inside the opening 130. The pin jack 113 is fixed to the intermediate wall 132 of the major body portion 103A and connected to the circuit board 107.

The lid 103B, as shown in FIG. 15 and FIG. 18, includes a lid-side contact point 112 contacting the electrode of the battery 101 loaded in the major body portion 103A. The illustrated lid 103B includes an insertion tube 140 inserted into the opening 130 of the major body portion 103A, and also includes lid-side contact points 112 contacting the other electrode of the two batteries 101 loaded in the storage portion 105, at opposite sides of a distal surface of the insertion tube 140. Further, the lid 1038 is provided, between lid-side contact points 112, with an exposed pin terminal 114 for connection with the inserted pin jack 113. Although not shown, the lid-side contact point 112 and the pin terminal 114 are fixed to the circuit board 108 incorporated in the lid, with a structure as disclosed in FIG. 3 according to the above-mentioned embodiment.

In the above-described interior casing 103, the battery 101 is accommodated in a given place of the interior casing 103 by loading the battery 101 in the storage portion 105 of the major body portion 103A and by attaching the lid 103B to the opening 130 of the major body portion 103A. In particular, by closing the opening 130 of the major body portion 103A by the lid 1038, the opposite electrodes of the battery 101 are pressed from opposite sides between the lid-side contact point 112 of the lid 103B and the case-side contact point 111 of the major body portion 103A to electrically connect the battery 101 to the contact points. Further, the interior casing 103 electrically connects the major body portion 103A and the lid 1038 via the pin jack 113. In the interior casing 103 with the structure as disclosed in the FIG. 3 according to the above-described embodiment, when the lid 1038 is inserted to the major body portion 103A for closure, the pin jack 113 protruding from the intermediate wall 132 is inserted into the pin terminal 114 provided on the insertion tube 140 to achieve a mutual connection. The structure is so simplified as to enable the major body portion 103A and the lid 103B to be detachably connected for achieving an electrical connection.

Further, regarding the interior casing 103, in order to dispose the heaters 104, in a thermally connected state, on the inner sides of the planar surface 102C being the opposite surfaces of the metallic exterior casing 102, a recess 103*d* is provided, on opposite sides of the major body portion 103A, i.e., on the outer surfaces of the major body case portion 103*a* and lid case portion 103*b*, and the holder plate 106 for positioning and fixing the heater 104 is fixed to the recess 103*d*. Regarding the major body portion 103A, the heater 104 is disposed, for thermal connection, on the inner surface of the planar surface 102C of the metallic exterior casing 102 via the holder plate 106 fixed to the recess 103*d*. In the illustrated pocketable body warmer, a thermal influence on the battery 1 is reduced by disposing, via the holder plate 106 and major body portion 103A, the heater 104, which is disposed inside the planar surface 102C of the metallic exterior casing 102, between two batteries 101 loaded in the storage portion 105.

Electric power is supplied to the heater 104 by allowing a metal plate 155, 156 to contact the electrode surface on opposite faces in an elastically pressed state. The metal plate 155, 156, as shown in FIG. 16 through FIG. 20, has a connection piece 155A, 156A and an elastic piece 155B, 156B protruded around the disk contacting the electrode surface of the heater 104. The connection piece 155A, 156A is connected via a lead wire (not shown) to the circuit board 107 for electrification. The elastic piece 155B, 156B, balanced around the disk, is disposed at a position opposite to the disk as viewed in the drawing. In the metal plate 155 disposed on the back surface of the heater 104, that is, on the side of the interior casing 103, the disk is elastically pressed by the elastic piece 1558 to the electrode surface of the heater 104, and the heater 104 is pressed to the inner surface of the planar surface 102C of the metallic exterior casing 102. In the metal plate 156 disposed between the heater 104 and the metallic exterior casing 102, the tip of the elastic piece 1568 is inserted into the integrally formed engagement portion 166 disposed on the surface of the holder plate 106; and the metal plate 155, the heater 104, and the metal plate 156 on the side of the interior casing 103 are connected respectively to a given position of the holder plate 106. Further, in order to dispose a stack of the metal plate 155, the heater 104 and the metal plate 156 in a given position, an integrally formed positioning rib 163 is provided on the surface of the holder plate 106. The positioning rib 163 is provided with a cutout portion 163A for guiding the elastic piece 1558 and the connection piece 155A of the metal plate 155 disposed between the heater 104 and the holder plate 106. The elastic piece 1558 and the connection piece 155A are guided to the cutout portion 163A of the positioning rib 163, and the stack of the disk of the metal plate 155 and the heater 104 is disposed inside the positioning rib 163. Such a structure enables the metal plate 155 and the heater 104 to be disposed on the surface of the holder plate 106 so as not to be displaced. In this state, the heater 104 composed of the PTC element 104A is inserted into the metallic exterior casing 102 and disposed on the inner surface of the metallic exterior casing 102 in a thermally connected state. The heaters 104 being thermally connected to the opposite surfaces of the metallic exterior casing 102 allow the generated heat to be conducted via the metal plate 156 to the planar surface 102C on opposite surfaces, and the entire surface of the metallic exterior casing 102 is heated.

Further, the illustrated pocketable body warmer has a temperature sensor 152 proximately to or in contact with the inner side of the metallic exterior casing 102. The temperature sensor 152 shown in FIG. 16 through FIG. 18 respectively passes through a through hole 103*e* of the interior casing 103 and a through hole 106*a* of the holder plate 106, and the tip of the sensor is disposed in a positioning recess 103*f* provided outside the interior casing 103. In this arrangement, a temperature sensing portion of the temperature sensor 152 is disposed proximately to or in contact with the metallic exterior casing 102 to be in a thermally connected state with the metallic exterior casing 102. In this structure, when the temperature sensor 152 is proximate to or in contact with the inner side of the metallic exterior casing 102, the temperature sensor 152 can sensitively detect the outer temperature, especially low-temperature open air and a cooled portion (such as hands) of the human body. Therefore, it is possible to quickly detect whether a temperature decrease or a descending gradient becomes larger than a predetermined value, in other words, whether temperature decrease is more than a predetermined temperature in a given period of time. Thus, the power supplied from the battery can be controlled as is controllable within a temperature range based on each mode as will be described below.

Figure 21:
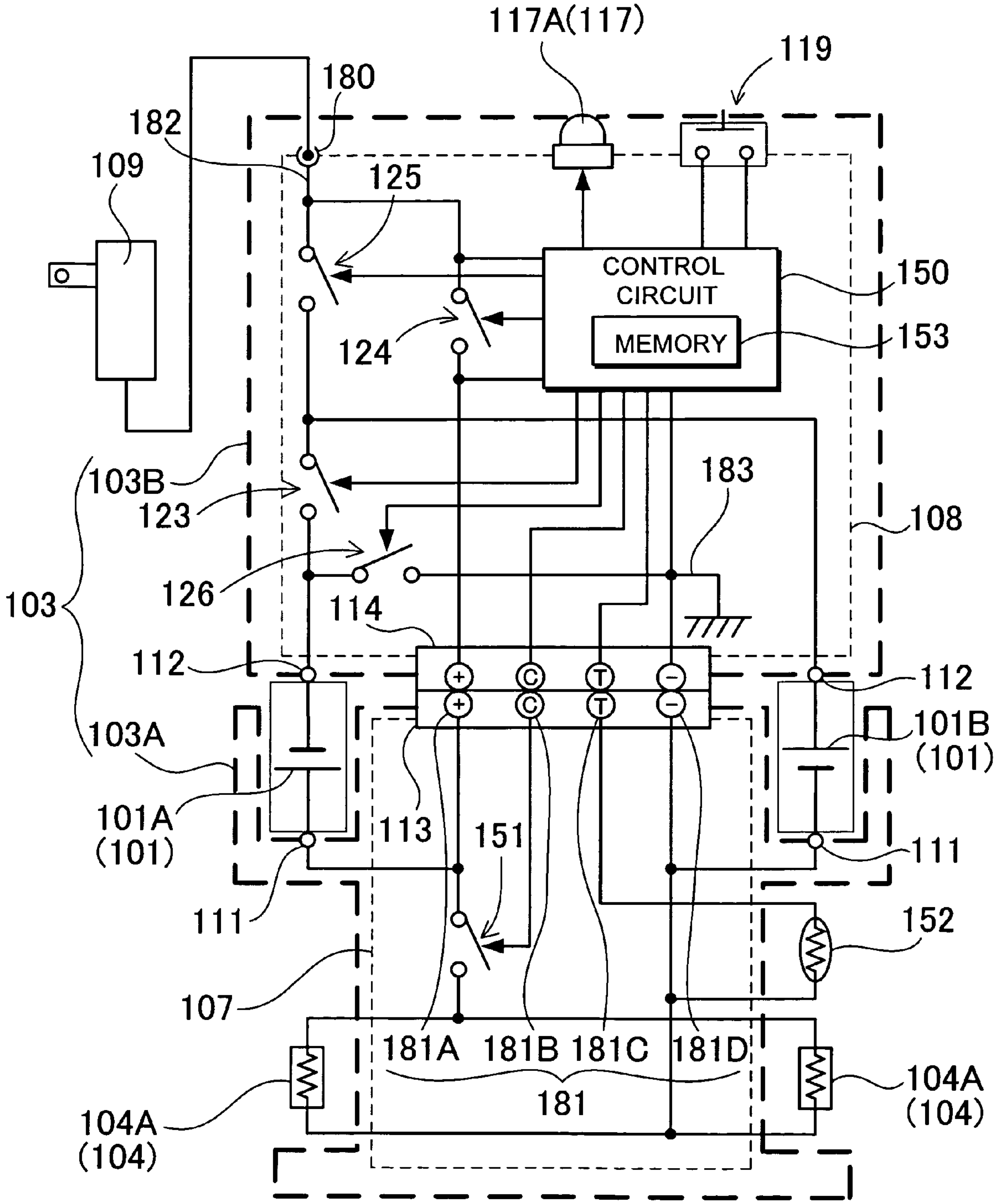
FIG. 21 is a circuit diagram of the pocketable body warmer in accordance with even another embodiment of the present invention.

FIG. 21 is a circuit diagram of the above-described pocketable body warmer. The pocketable body warmer shown in this diagram includes two pieces of heaters 104 mutually connected in parallel, two pieces of batteries 101 supplying electric power to the heater 104, the control circuit 150 controlling the power supplied from the batteries 101 to the heaters 104, and the temperature sensor 152 detecting the temperature of the metallic exterior casing 102. The illustrated pocketable body warmer has the control circuit 150 mounted to the circuit board 108 incorporated in the lid 1038 of the interior casing 103, connects two pieces of heater 104 and the temperature sensor 152 to the circuit board 107 incorporated in the major body portion 103A, and further connects one of the electrodes of the two batteries 101 to the circuit board 107 via the case-side contact point 111 and the other of the electrodes to the circuit board 108 via the lid-side contact point 112. Further, in the illustrated pocketable body warmer, the circuit board 107 of the major body portion 103A and the circuit board 108 of the lid 103B are electrically connected together via the pin jack 113 and the pin terminal 114. The pin jack 113 and the pin terminal 114 shown in FIG. 21 include four pieces of connection terminals 181, which will be described below in detail.

In the illustrated pocketable body warmer, the heaters 104 being the PTC elements 104A are parallel-connected to reduce the electric resistance and to increase power consumption, that is, an amount of heat generation. For example, when the electric resistance of the heater 104 composed of each PTC element 104A is 1Ω, and when a total voltage of the batteries 1 mutually connected in series is 2.4 V, the power consumption of the heater 104 increases up to 11.5 W. Therefore, in a state of electrifying the heater 104, two pieces of PTC elements 104A can quickly heat up the metallic exterior casing 102 from inside.

Regarding the two pieces of batteries 101, the electrodes connected to the lid-side contact points 112 are mutually series-connected via the switching element 123, while the electrodes connected to the case-side contact points 111 are mutually series-connected via the switching element 151 mounted on the circuit board 107 and the parallel-connected heaters 104. The switching elements 123, 151 are controlled to switch on/off by the control circuit 150, and the electrification to the heaters 104 are controlled. The switching element 151 mounted on the circuit board 107 is connected to the control circuit 150 via the control terminal 181B belonging to the connection terminal 181 composed of the pin jack 113 and the pin terminal 114. In the pocketable body warmer, when the control circuit 150 controls both of the switching elements 123, 151 to be switched on, the two pieces of batteries 101 are series-connected to electrify the two pieces of heaters 104. Further, when the control circuit 150 controls both of or either one of the switching elements 123, 151 to be switched off, the electrification from the batteries 101 to the heaters 104 is stopped. That is to say, the control circuit 150 controls the switching elements 123, 151 electrifying the heaters 104 to be switched on/off and controls to maintain the surface temperature of the metallic exterior casing 102 at the predetermined temperature.

Further, the control circuit 150 stores a plurality of predetermined temperature information in the memory 153. The memory 153 stores, for example, predetermined temperature information for a turbo mode, a strong mode, and a weak mode. The predetermined temperature information stored in the memory 153 are higher in the order of the turbo mode, the strong mode, and the weak mode; for example, with the turbo mode being set at 45° C. to 53° C., the strong mode at 38° C. to 43° C., and the weak mode at 35° C. to 38° C. Further, the control circuit 150 also stores in the memory 153 a period of turbo time to retain the metallic exterior casing 102 at a predetermined temperature in the turbo mode. The period of time to continue the turbo mode is set to be, for example, 3 to 10 minutes, preferably 4 to 8 minutes.

The power on/off, the turbo mode, the strong mode and the weak mode can be turned by a press button switch 119 connected to the control circuit 150. For example, every time when the press button switch 119 is pressed one time, the mode is changed to the strong mode, the weak mode and the power off; when the press button switch 119 continues to be pressed for a given period of time (namely, press-and-hold), the mode is turned to the turbo mode. The control circuit 150 detects the descending gradient of the temperature of the metallic exterior casing 102 by receiving the signal inputted from the temperature sensor 152 via a temperature detection terminal 181C belonging to the connection terminal 181 composed of the pin jack 113 and the pin terminal 114. So, when the descending gradient is larger than a predetermined value, for example, when the temperature decrease is over 2° C. for 3 seconds, the mode can be switched to the turbo mode. Further, when the control circuit 150 detects the temperature of the metallic exterior casing 102 to find that the detected temperature is lower than a predetermined value, the mode can also be turned to the turbo mode.

Further, the pocketable body warmer shown in FIG. 21 is so structured as to use secondary batteries as the batteries 101 loaded in the major body portion 103A, with the batteries 101 being rechargeable. The illustrated pocketable body warmer is provided with an external power terminal 180 for a recharging operation (structured like the connection terminal 15 as disclosed in FIG. 3 according to the above-described embodiment), and is connected via the external power terminal 180 to an external apparatus such as a charger to recharge the batteries 101 loaded inside. The pocketable body warmer shown in FIG. 21 is provided with the external power terminal 180 at the lid 103B, with an AC adaptor 109 being connected to the external power terminal 180. The illustrated pocketable body warmer is so structured that the switching elements 151, 123, 124, 125, 126 are controlled by the control circuit 150, and each of the batteries 101A, 101B can be individually charged. In the illustrated pocketable body warmer, the power line 182 connected to the external power terminal 180 is branched into two lines, with one of the lines being connected to the positive side of the battery 101A via the switching element 124 and via the power terminal 181A belonging to the connection terminal 181 composed of the pin jack 113 and the pin terminal 114, and with the other of the lines being connected to the positive side of the battery 101B via the switching element 125. Further, the negative side of the battery 101A is connected via the switching element 126 to a grounding line 183, while the negative side of the battery 101B is connected to the grounding line 183 via a grounding terminal 181D belonging to the connection terminal 181 composed of the pin jack 113 and the pin terminal 114. In the pocketable body warmer, when the battery 101A is charged, the control circuit 150 turns the switching elements 151, 123, 125 to be switched off and the switching elements 124, 126 to be switched on. Likewise, when the battery 101B is charged, the control circuit 150 turns the switching elements 151, 123, 124, 126 to be switched off and the switching element 125 to be switched on. Further, the control circuit 150 incorporates a circuit for detecting respective residual capacity of the batteries 101A, 101B on the basis of integrated values of the battery voltage and charging/discharging current. When the battery 101A is fully charged, the switching elements 124, 126 are turned off to stop the charging operation; and when the battery 101B is fully charged, the switching element 125 is turned off to stop the charging operation.

The above-described pocketable body warmer is so structured as to use secondary batteries as the batteries 101 loaded in the major body portion 103A, with the batteries 101 being rechargeable. It should be noted that the secondary battery can be replaced with the primary battery. Since the primary battery is not to be recharged, a measure is taken for avoiding a mistaken charging operation; a function is provided for stopping a charging operation by detecting a primary battery that is loaded, which is possible when the control circuit 150 measures the battery voltage, etc. when the charging power is to be supplied. Further, the pocketable body warmer does not necessarily have to be so structured as to charge a battery loaded in the body warmer. In the pocketable body warmer, electronic components such as a switching element for charging a battery do not have to be mounted to the circuit board on the lid, and a connection terminal is not needed for the circuit board of the major body portion to be connected to the power line and the grounding line in the lid. Therefore, in this pocketable body warmer, the circuit board can be simplified, and the cost of manufacturer can be reduced by using a less expensive pin jack and pin terminal having only two connection terminals.

Further, the control circuit 150 incorporates a circuit for detecting the residual capacity of the battery 101 on the basis of the integrated values of the battery voltage and charging/discharging current, and when the power is switched off, the residual capacity of the battery 101 is to be displayed for a certain period of time. In order to display the residual capacity and the operation mode, the control circuit 150 is connected with the display 117 having LED 117A. In the display 117, the strong mode is indicated by a blinker in a red color, the weak mode is indicated by a blinker in an orange color, and when the residual capacity is to be indicated after the power is switched off, the residual capacity is indicated by a lighting state of the LED 117A. For example, the large, medium and small residual capacity are indicated in the order of a continued green lighting, a slow blinking, and a quick blinking.

It should be apparent to those of ordinary skill in the art that while various preferred embodiments of the invention have been shown and described, it is contemplated that the invention is not limited to the particular embodiments disclosed, which are deemed to be merely illustrative of the inventive concepts and should not be interpreted as limiting the scope of the invention, and which are suitable for all modifications and changes falling within the scope of the invention as defined in the appended claims. The present application is based on Application No. 2007-182502 filed in Japan on Jul. 11, 2007, and No. 2008-158557 filed in Japan on Jun. 17, 2008, the contents of which are incorporated herein by references.

What is claimed is:

1. A pocketable body warmer comprising:

a metallic exterior casing formed in the shape of a tube, the metallic exterior casing having a closed bottom end, an open opposite end, and a metal plate disposed near the closed bottom end;

a plastic interior casing inserted in the metallic exterior casing, the plastic interior casing being provided with an interior battery storage portion and having an outer contour that conforms to an interior peripheral surface of the metallic exterior casing;

at least one battery loaded in the interior battery storage portion of the plastic interior casing; and at least one heater thermally connected to the metallic exterior casing for heating the metallic exterior casing, wherein the plastic interior casing comprises a body portion fixed to the metallic exterior casing and a lid connected to the body portion for closing the open opposite end of the metallic exterior casing.

2. The pocketable body warmer as recited in claim 1, wherein the battery is detachably loaded in the plastic interior casing.

3. The pocketable body warmer as recited in claim 1, wherein the plastic interior casing is made of a plastic material having a smaller thermal conductivity than that of the metallic exterior casing.

4. The pocketable body warmer as recited in claim 1, wherein the at least one battery comprises two batteries loaded in a mutually parallel relationship, the body portion is provided with a board storage portion located between the two batteries, and the board storage portion has a circuit board disposed therein.

5. The pocketable body warmer as recited in claim 4, wherein the circuit board is connected to the batteries and the heater, the circuit board including a circuit for controlling a power supply to the heater.

6. The pocketable body warmer as recited in claim 2, wherein the battery is an AA size battery.

7. The pocketable body warmer as recited in claim 1, wherein the lid is detachably connected to the body portion to enable the battery to be replaced by detaching the lid.

8. The pocketable body warmer as recited in claim 1, wherein the lid comprises: an insertion tube inserted into an opening of the body portion; and a flange connected to an end of the insertion tube to close the opening of the body portion and the open opposite end of the metallic exterior casing.

9. The pocketable body warmer as recited in claim 8, wherein the flange is cap-shaped with a peripheral wall disposed around a top plate serving as an operation surface.

10. The pocketable body warmer as recited in claim 8, wherein the plastic interior casing comprises a positioning mechanism for preventing the insertion tube from being inserted into the body portion in a wrong orientation.

11. The pocketable body warmer as recited in claim 1, wherein the heater is a PTC element, the PTC element being disposed at the bottom of the metallic exterior casing.

12. The pocketable body warmer as recited in claim 1, wherein:

the heater is disposed between the metallic exterior casing and the plastic interior casing;

a holder plate is disposed between the plastic interior casing and the heater;

the heater is interposed between the holder plate and an inner surface of the metallic exterior casing to thermally connect the heater to the metallic exterior casing; and a gap is defined between the holder plate and the plastic interior casing, thus restraining thermal conduction from the heater to the plastic interior casing.

13. The pocketable body warmer as recited in claim 1, wherein the battery is a nickel-hydrogen battery.

14. The pocketable body warmer as recited in claim 1, wherein the battery is a rechargeable battery, and the pocketable body warmer includes a charging circuit for charging the battery.

15. The pocketable body warmer as recited in claim 1, further comprising:

a switching element connected between the battery and the heater;

a control circuit for controlling the switching element to be switched on/off to control electric power supplied from the battery to the heater; and a temperature sensor for detecting the temperature surrounding the battery.

16. The pocketable body warmer as recited in claim 15, wherein the body portion of the plastic interior casing is fixed to the metallic exterior casing, and the lid is detachably connected to the body portion, and the control circuit comprises:

a first control sub-circuit mounted to a first circuit board incorporated in the lid of the plastic interior casing; and a second control sub-circuit mounted to a second circuit board incorporated in the body portion of the plastic interior casing, wherein the first control sub-circuit mounted to the first circuit board and the second control sub-circuit mounted to the second circuit board are connected together via a pin jack and a pin terminal.

17. The pocketable body warmer as recited in claim 15, wherein the control circuit incorporates a memory for storing a state of predetermined temperature, and the control circuit controls duty of switching on/off the switching element so as to allow the heater to reach a level of the predetermined temperature stored in the memory.

18. The pocketable body warmer as recited in claim 17, wherein the memory in the control circuit stores the states of the predetermined initial temperature and the predetermined normal temperature, and the predetermined initial temperature is set to be higher than the predetermined normal temperature.

19. The pocketable body warmer as recited in claim 17, wherein, in the control circuit, the heater is heated up to the predetermined initial temperature at an initial stage of switching on a power switch of the pocketable body warmer, followed by controlling the heater to be maintained at the predetermined normal temperature.

20. The pocketable body warmer as recited in claim 1, wherein the heater is disposed inside opposite surfaces of the metallic exterior casing.

21. The pocketable body warmer as recited in claim 20, wherein the interior casing has a recess defined on an outer surface of the body portion; the recess has a holder plate fixed thereto; the heater is fixed to the holder plate; and the heater is disposed, for thermal connection, on an inner surface of a planar portion of the metallic exterior casing via the holder plate.

22. The pocketable body warmer as recited in claim 4, wherein the interior casing has a first recess formed in an outer surface of a side of the body portion and a second recess formed in an outer surface of an opposite side of the body portion;

wherein the first recess has a holder plate fixed thereto;

wherein the heater is positioned and fixed to the holder plate; and the heater is disposed, for thermal connection, on an inner surface of a planar portion of the metallic exterior casing via the holder plate, and wherein the heater disposed inside the metallic exterior casing is disposed, via the holder plate and the body portion, between the two batteries loaded in a storage portion.

23. The pocketable body warmer as recited in claim 20, wherein electric power is supplied to the heater by allowing a metal plate to contact an electrode surface on opposite faces in an elastically pressed state; the metal plate has an elastic piece protruded therearound; and the heater is pressed by the elastic piece to the inner surface of the planar portion of the metallic exterior casing.

24. The pocketable body warmer as recited in claim 20, further comprising a control circuit for controlling the electric power supplied to the heater, wherein the control circuit stores a plurality of predetermined temperature information in a memory.

25. The pocketable body warmer as recited in claim 24, wherein the memory stores predetermined temperatures for a turbo mode, a strong mode, and a weak mode, and the predetermined temperatures are higher in the order of the turbo mode, the strong mode, and the weak mode.

26. The pocketable body warmer as recited in claim 25, wherein the predetermined temperature for the turbo mode is set at 45° C. to 53° C., the predetermined temperature for the strong mode is set at 38° C. to 43° C., and the predetermined temperature for the weak mode is set at 35° C. to 38° C.

27. The pocketable body warmer as recited in claim 24, wherein the control circuit stores, in the memory, a period of turbo time to retain the metallic exterior casing at the predetermined temperature in a turbo mode.

28. The pocketable body warmer as recited in claim 27, wherein the period of turbo time to continue the turbo mode is set to be 3 to 10 minutes.

29. The pocketable body warmer as recited in claim 25, wherein a press button switch is connected to the control circuit, and the power on/off, the turbo mode, the strong mode and the weak mode are selected by the press button switch.

30. The pocketable body warmer as recited in claim 29, wherein the press button switch is pressed to turn the mode to the strong mode, the weak mode and the power off, and when the press button switch continues to be pressed for a given period of time, the mode is turned to the turbo mode.

31. The pocketable body warmer as recited in claim 1, wherein a temperature sensor is disposed proximately to or in contact with the interior peripheral surface of the metallic exterior casing.

32. The pocketable body warmer as recited in claim 1, wherein the lid is detachably connected to the body portion, and wherein the body portion and the lid are electrically connected together via a pin jack.

33. The pocketable body warmer as recited in claim 10, wherein the lid is provided with a lid-side contact point in contact with an electrode of the battery loaded in the body portion.

34. The pocketable body warmer as recited in claim 1, wherein, when the body portion is inserted in the metallic exterior casing and the lid closes the open opposite end of the metallic exterior casing, part of the lid is exposed exteriorly of the metallic exterior casing.

35. The pocketable body warmer as recited in claim 1, wherein the battery is completely surrounded by the plastic interior casing and the metallic exterior casing such that the interior and exterior casings form a double wall structure.

* * * * *